(12) United States Patent
Blum et al.

(10) Patent No.: US 9,238,661 B2
(45) Date of Patent: Jan. 19, 2016

(54) ORGANOBORON COMPOUNDS AND METHODS OF MAKING ORGANOBORON COMPOUNDS

(71) Applicant: The Regents of the University of California, Oakland, CA (US)

(72) Inventors: Suzanne A. Blum, Irvine, CA (US); Joshua J. Hirner, Irvine, CA (US); Darius J. Faizi, Oceanside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/303,684

(22) Filed: Jun. 13, 2014

(65) Prior Publication Data

US 2014/0371444 A1    Dec. 18, 2014

Related U.S. Application Data

(60) Provisional application No. 61/836,391, filed on Jun. 18, 2013, provisional application No. 61/906,040, filed on Nov. 19, 2013.

(51) Int. Cl.
*C07F 5/02* (2006.01)

(52) U.S. Cl.
CPC .................. *C07F 5/027* (2013.01); *C07F 5/025* (2013.01)

(58) Field of Classification Search
CPC ................................ C07F 5/025; C07F 5/027
USPC ......................................................... 544/69
See application file for complete search history.

(56) References Cited

PUBLICATIONS

King, Med. Chem., Principle and Practice (1994), pp. 206-208.*
Ibraheem A. I. Mkhalid, et al.; "C—H Activation for the Construction of C—B Bonds"; Durham University, Department of Chemistry, South Road, Durham, DH1 3LE, United Kingdom; Chem. Rev. 2010, 110, 890-931.
Gary A. Molander, et al.; "Organotrifluoroborates: Protected Boronic Acids That Expand the Versatility of the Suzuki Coupling Reaction"; Roy and Diana Vagelos Laboratories, Department of Chemistry, University of Pennsylvania, 231 South 34th Street, Philadelphia, Pennsylvania 19104-6323; Acc. Chem. Res. 2007, 40, 275-286.
Tatsuo Ishiyama, et al.; "Palladium(0)-Catalyzed Thioboration of Terminal Alkynes with 9-(Alkylthio)-9-borabicyclo[3.3. I]nonane Derivatives: Stereoselective Synthesis of Vinyl Sulfides via the Thioboration-Cross-Coupling Sequence"; Contribution from the Department of Applied Chemistry, Faculty of Engineering, Hokkaido University, Sapporo 060, Japan; J. Am. Chem. Soc. 1993, 115, 7219-7225.
Eric P. Gillis, et al.; "Multistep Synthesis of Complex Boronic Acids from Simple MIDA Boronates"; Roger Adams Laboratory, Department of Chemistry, UniVersity of Illinois at Urbana-Champaign, Urbana, Illinois 61801; 2 pages, published on the web Oct. 7, 2008.
R.H. Cragg; et al.; "Chloroboration and Allied Reactions of Unsaturated Compounds. Part 111.1 Aminoboration and Alkoxyboration of Isocyanates and Isothiocyanates"; Jan. 1, 1964; University of California—Irvine; 8 pages.
Noriyoshi Matsumi, et al.; Alkoxyboration Polymerization. Synthesis of Novel Poly(boronic carbamate)s; Department of Polymer Chemistry, Graduate School of Engineering, Kyoto University, Yoshida, Sakyo-ku, Kyoto 606-8501, Japan; Macromolecules 1998, 31, 3802-3806.

* cited by examiner

*Primary Examiner* — Taofiq A Solola
(74) *Attorney, Agent, or Firm* — Thomas Horstemeyer, LLP

(57) ABSTRACT

Embodiments of the present disclosure provide for methods of making an organoboron compound, organoboron compounds, and the like.

17 Claims, 9 Drawing Sheets

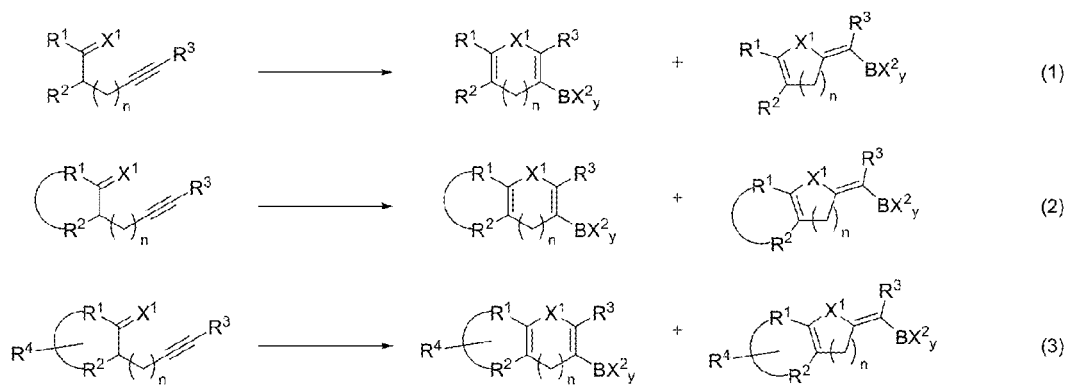
Fig. 1.1A
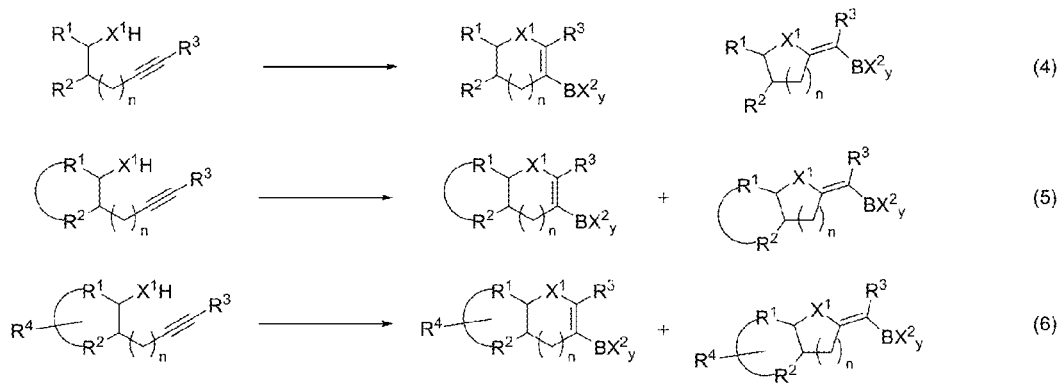
Fig. 1.1B

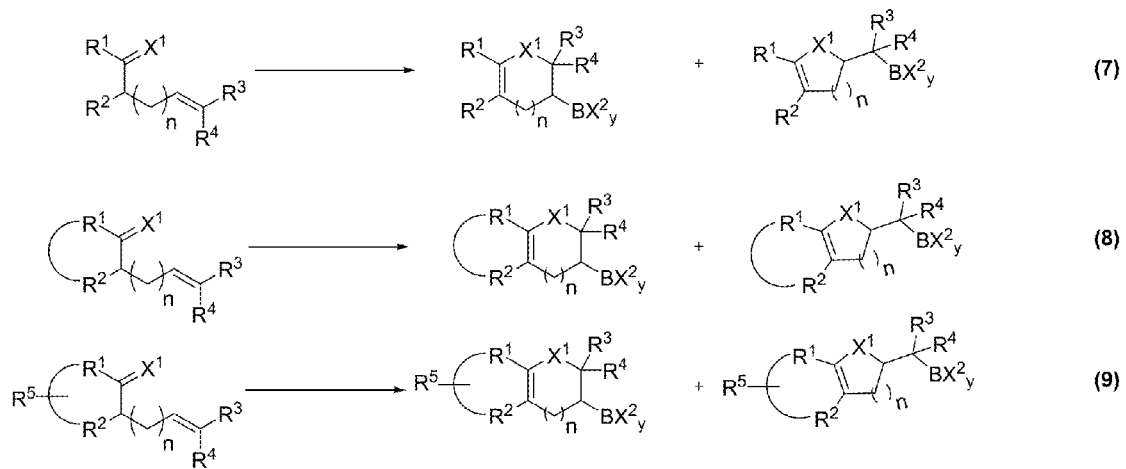
Fig. 1.1C
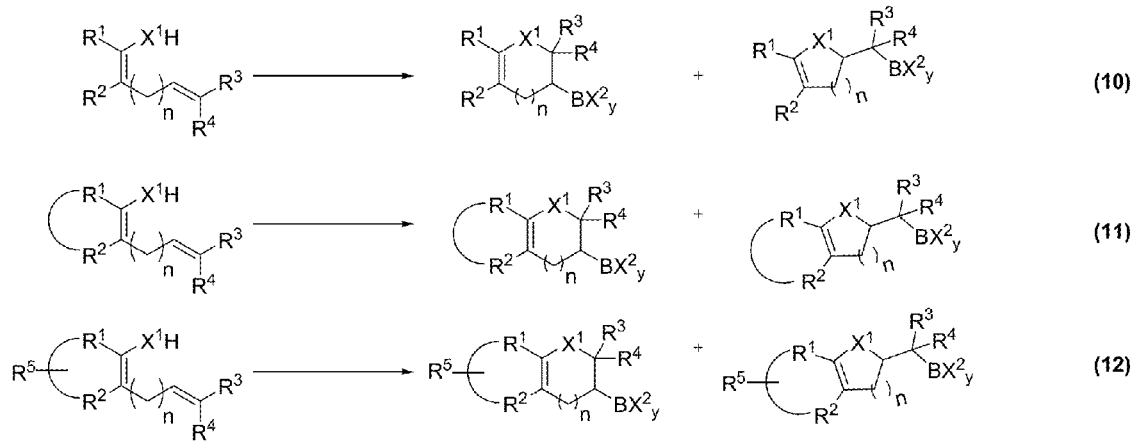
Fig. 1.1D

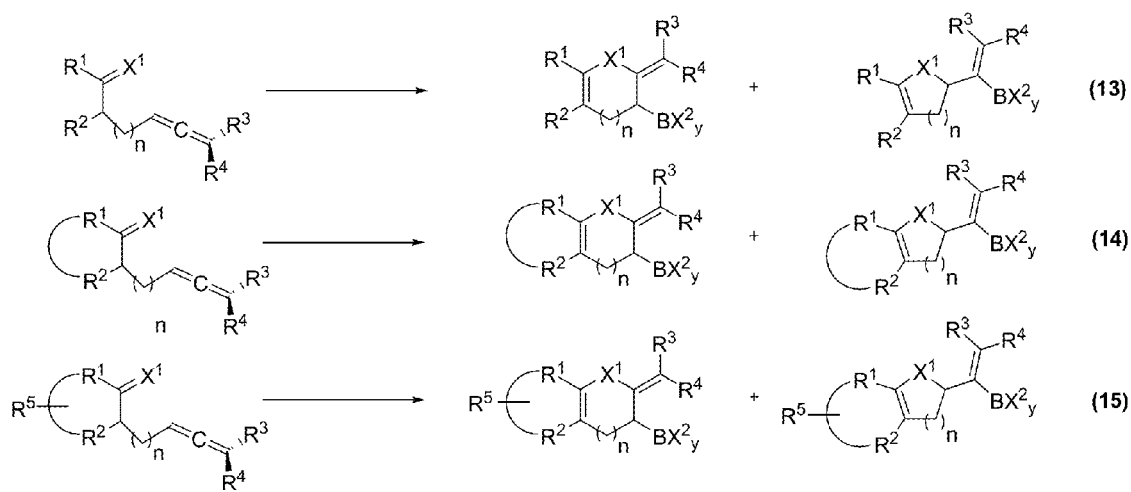
Fig. 1.1E
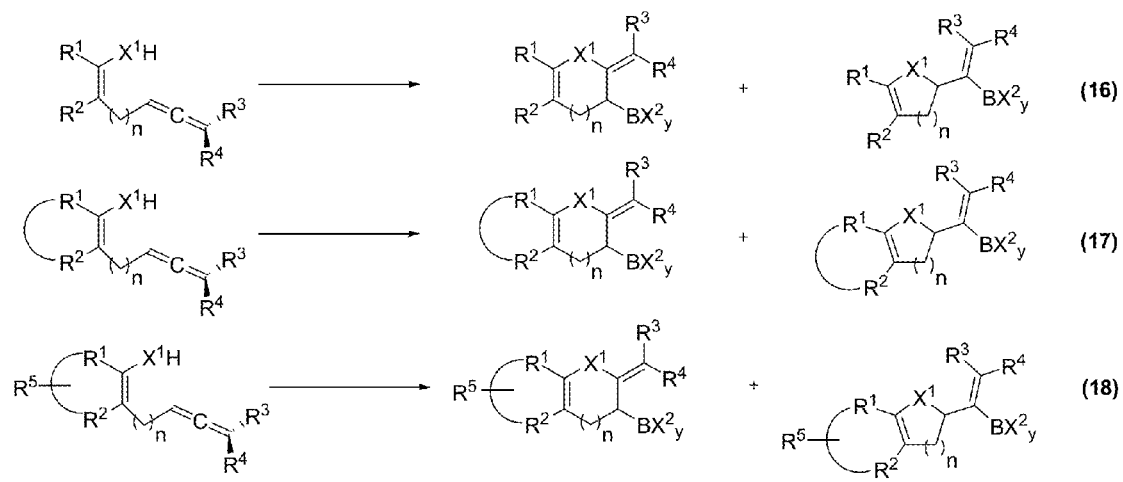
Fig. 1.1F

 (19)
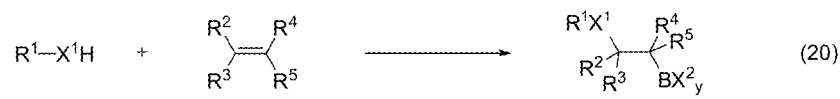 (20)
 (21)
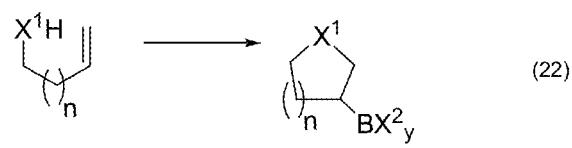 (22)
Fig. 1.1G
 (23)
 (24)
 (25)
E or Z
Fig. 1.1H

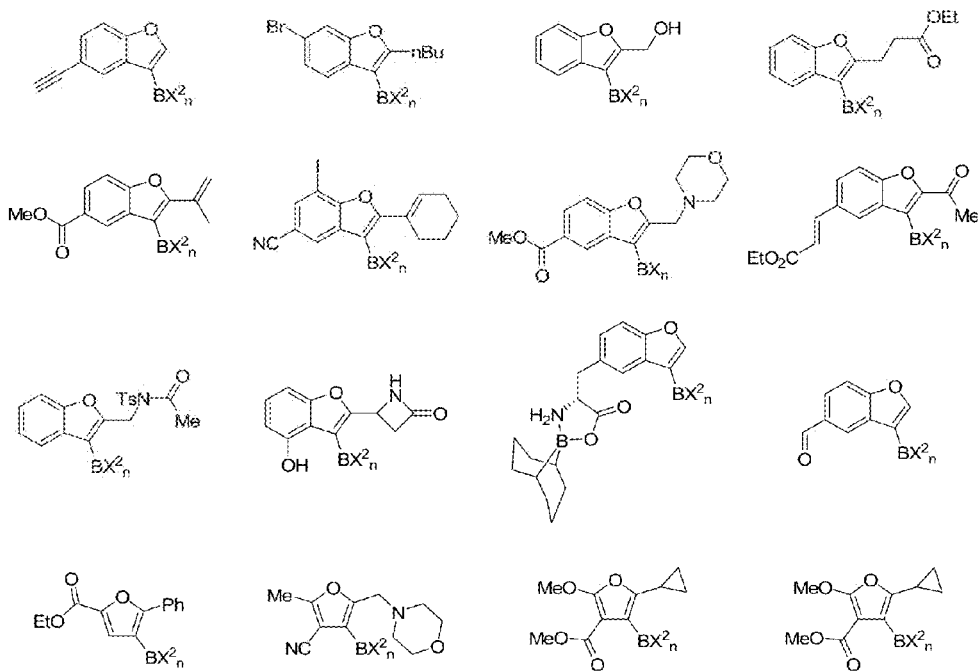
Fig. 1.2
Scheme 1. Optimized one-pot boric ester formation and alkoxyboration conditions
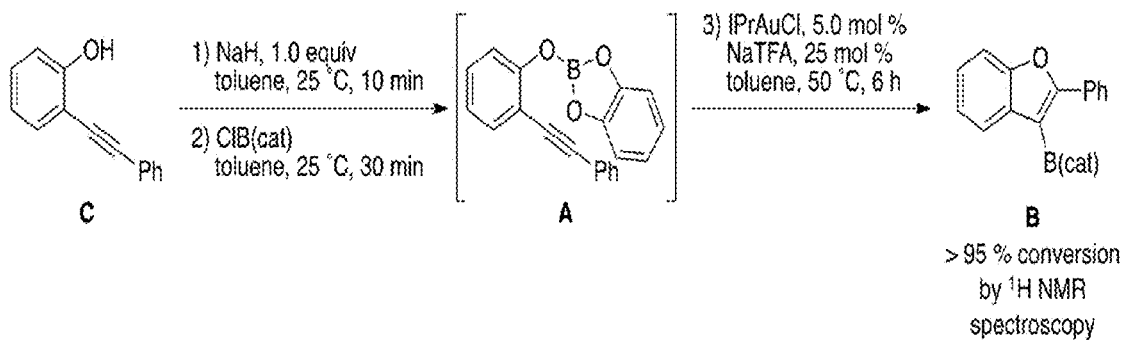
cat = catechol (1,2-dihydroxybenzene).
Fig. 1.3

Scheme 2. Methods for converting hydrolytically sensitive alkoxyboration product into moisture-stable analogs.
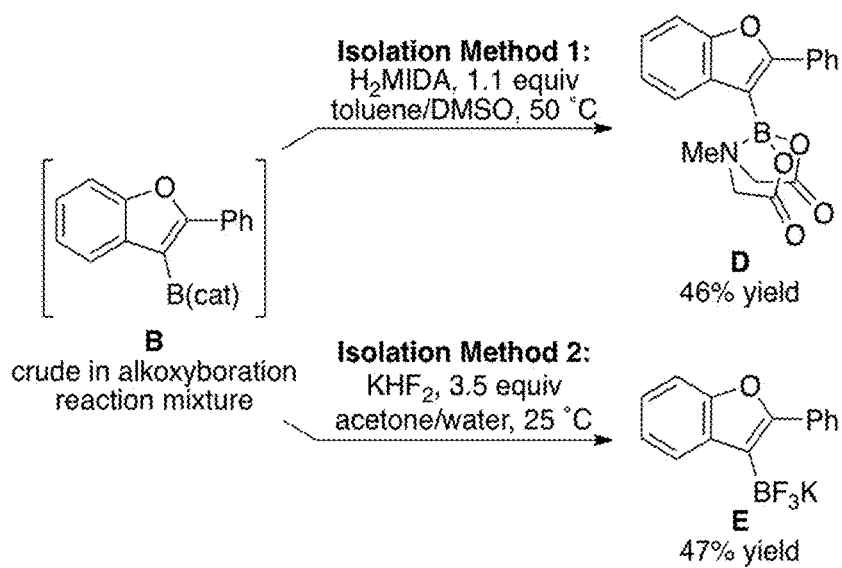
Fig. 1.4

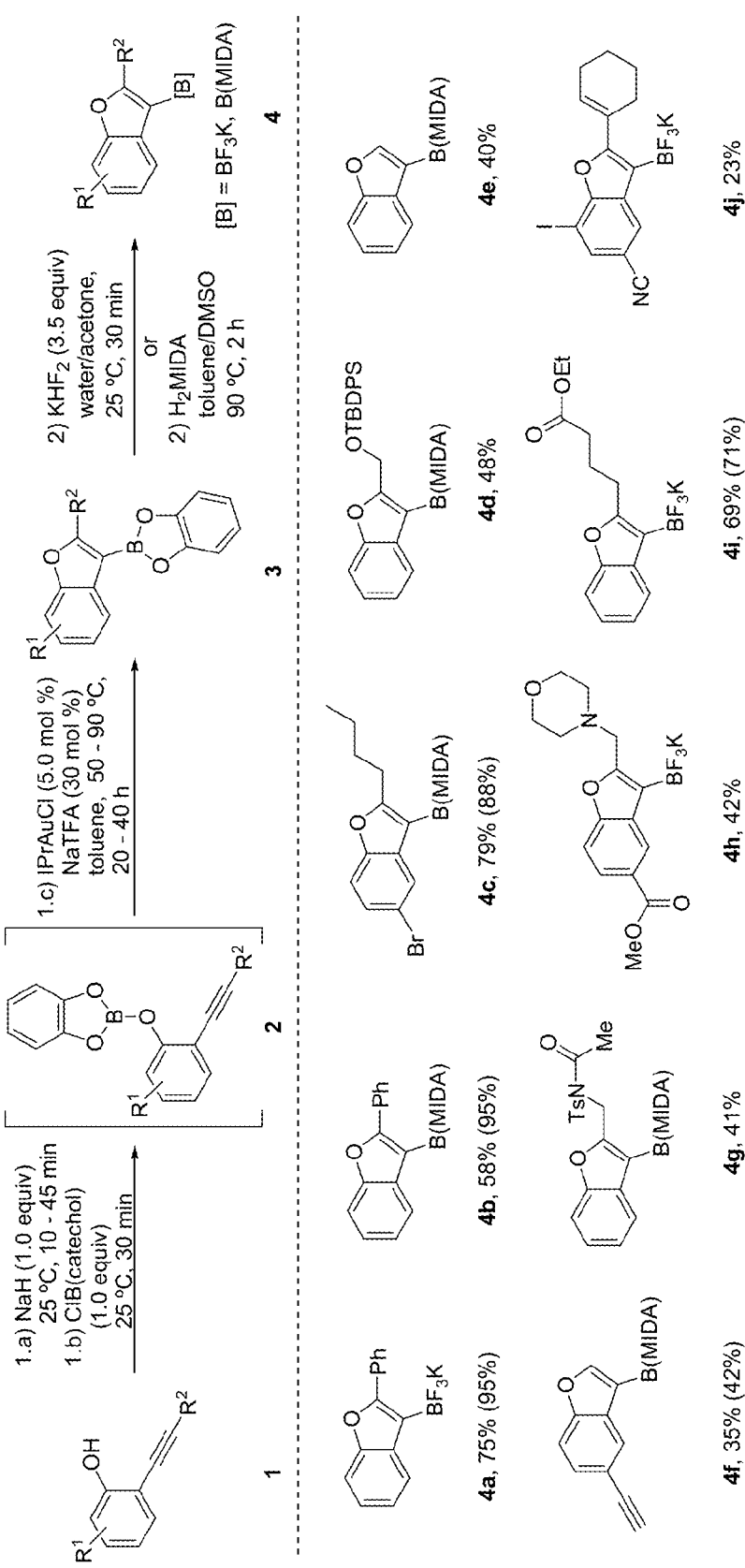
Fig. 1.5

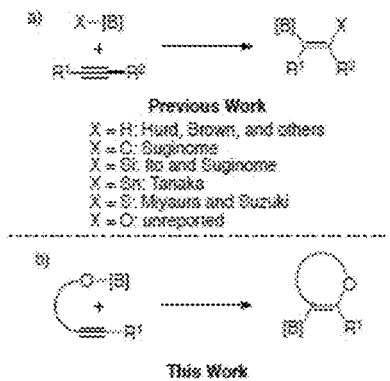
Fig. 2.1
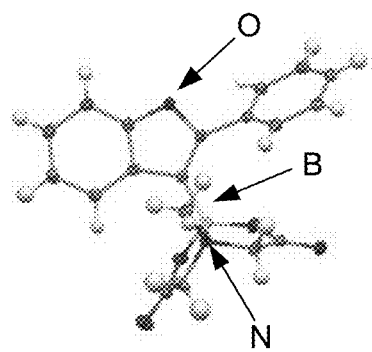
Fig. 2.2

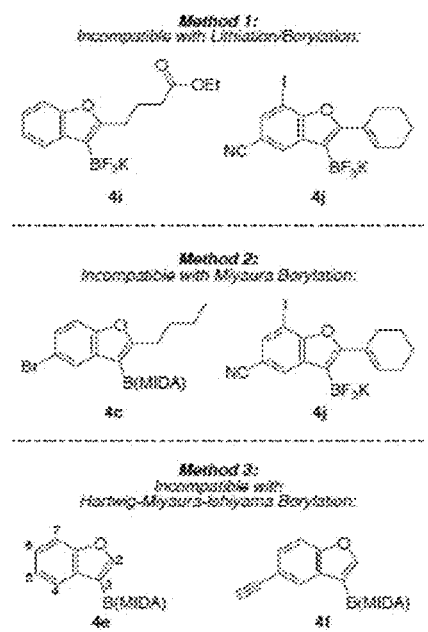
Fig. 2.3
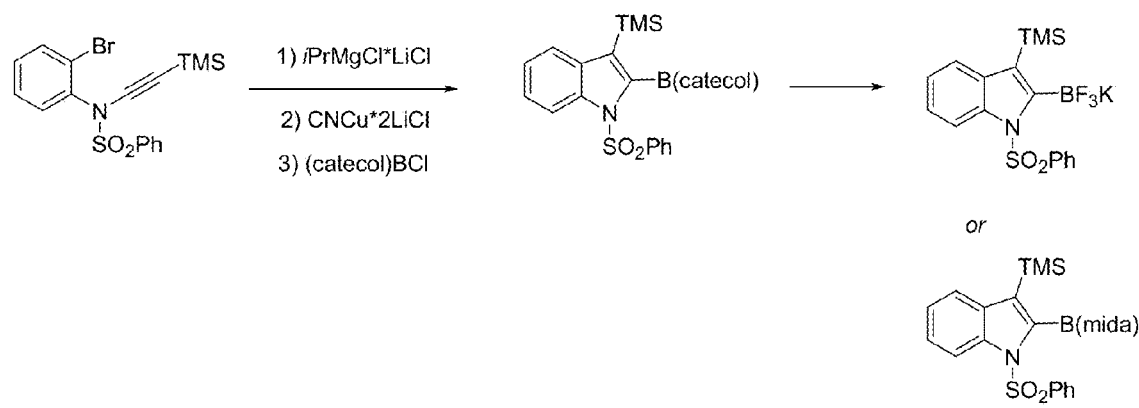
Fig. 3.1

ORGANOBORON COMPOUNDS AND METHODS OF MAKING ORGANOBORON COMPOUNDS

CROSS-REFERENCE TO RELATED APPLICATION

This application claims priority to U.S. provisional application entitled "BORONIC COMPOUNDS AND METHODS OF MAKING BORONIC COMPOUNDS," having Ser. No. 61/836,391, filed on Jun. 18, 2013, which is entirely incorporated herein by reference. This application also claims priority to U.S. provisional application entitled "BORONIC COMPOUNDS AND METHODS OF MAKING BORONIC COMPOUNDS," having Ser. No. 61/906,040, filed on Nov. 19, 2013, which is entirely incorporated herein by reference.

FEDERAL SPONSORSHIP

This invention was made with Government support under Contract/Grant No. 1R01GM098512-01, awarded by the National Institutes of Health. The Government has certain rights in this invention.

BACKGROUND

Since the initial report of a hydroboration reaction, the addition of H—B bonds to alkynes has become a widely-used reaction in organic synthesis. The resulting vinyl boranes are versatile intermediates for oxidation, copper-catalyzed conjugate addition, and Suzuki cross-coupling reactions. However, despite the widespread utility of the hydroboration reaction and development of many related X—B bond addition reactions (where X is a non-hydrogen atom), addition by some other types of boron bonds has not been reported.

SUMMARY

Embodiments of the present disclosure provide for methods of making an organoboron compound, organoboron compounds, and the like.

An exemplary embodiment of the present disclosure includes, among others, a method of making a organoboron compound, comprising a reaction described by one of the following schemes shown in the following figures: FIG. 1.1A (Schemes 1-3), FIG. 1.1B (Schemes 4-6), FIG. 1.1C (Schemes 7-9), FIG. 1.1D (Schemes 10-12), FIG. 1.1E (Schemes 13-15), FIG. 1.1F (Schemes 16-18), FIG. 1.1G (Schemes 19-22), and FIG. 1.1H (Schemes 23-25), where $X^1$ is O, N, S, or C where each of R, $R^1$, $R^2$, $R^3$, $R^4$, and $R^5$ are independently selected from: H, a carbonyl functional group, a carbocycle group, a heterocycle, a halide, or an alkyl group, where, optionally, $R^1$ and $R^2$ together with the carbon atoms they are attached to form a cyclic moiety, wherein $X^2$ is catecholate, pinacolate, ethylene glycolate, 1,3-propanediolate, N-methyliminodiacetate, 2,2'-azanediyldiethanolate, fluoride, or chloride, wherein n is 0 to 8, wherein y is from 1 to 3, where $X^3$ is C, O, N, or S, and where $X^4$ is a halogen, trifluoroacetic acid (TFA), tosylate (OTs), mesylate (OMs), or triflate (OTf); and where the reagent in each Scheme (1) to (25) is reacted with a salt of $BX^2$ and a Lewis acid metal catalyst to form the organoboron compound(s) shown in each Scheme (1) to (25).

An exemplary embodiment of the present disclosure includes, among others, a composition, comprising: an organoboron compound represented by one of the following structures:

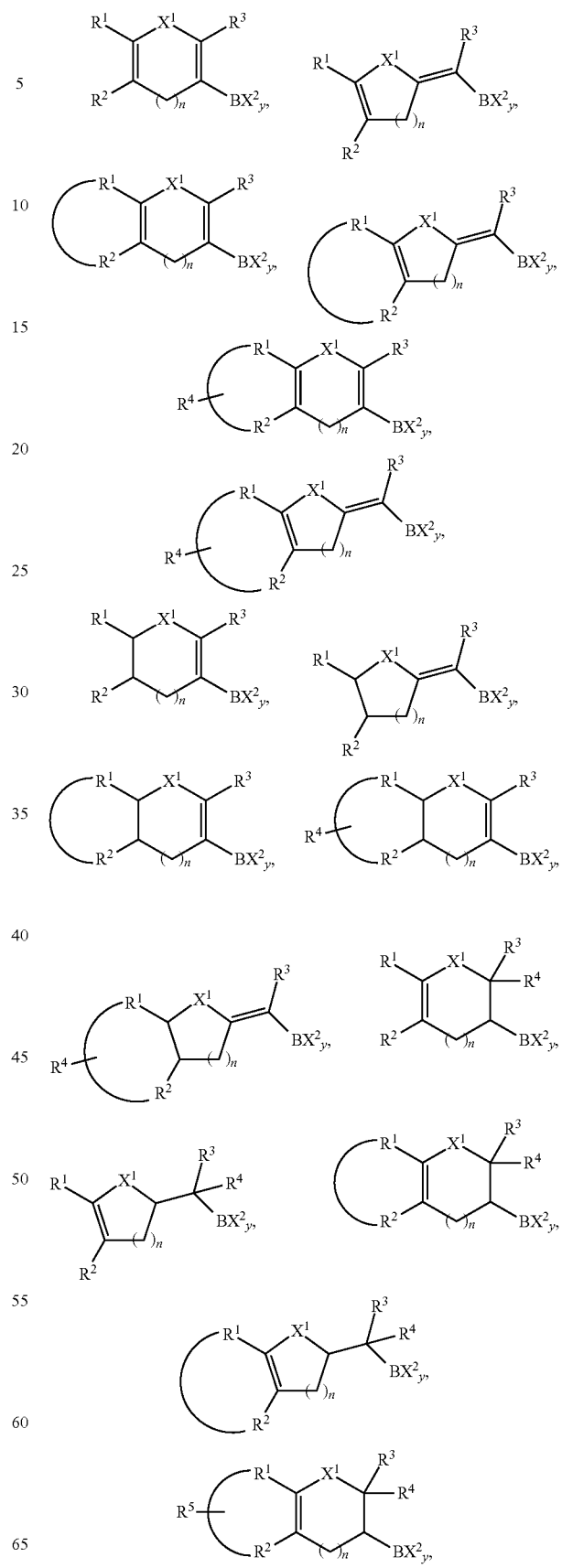

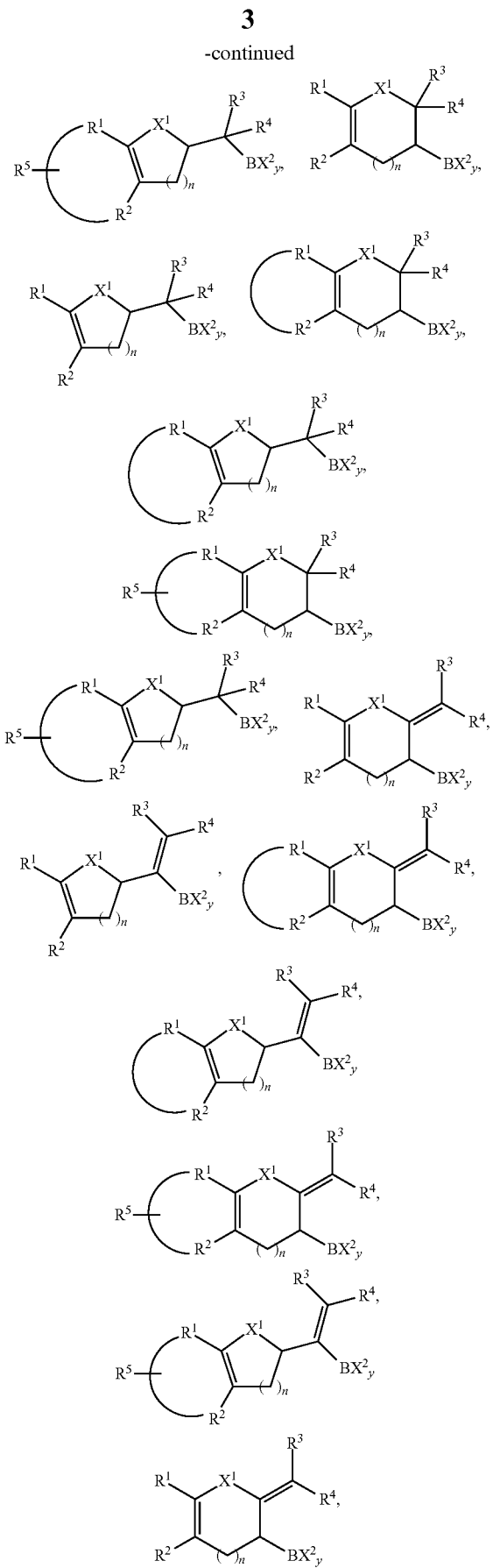
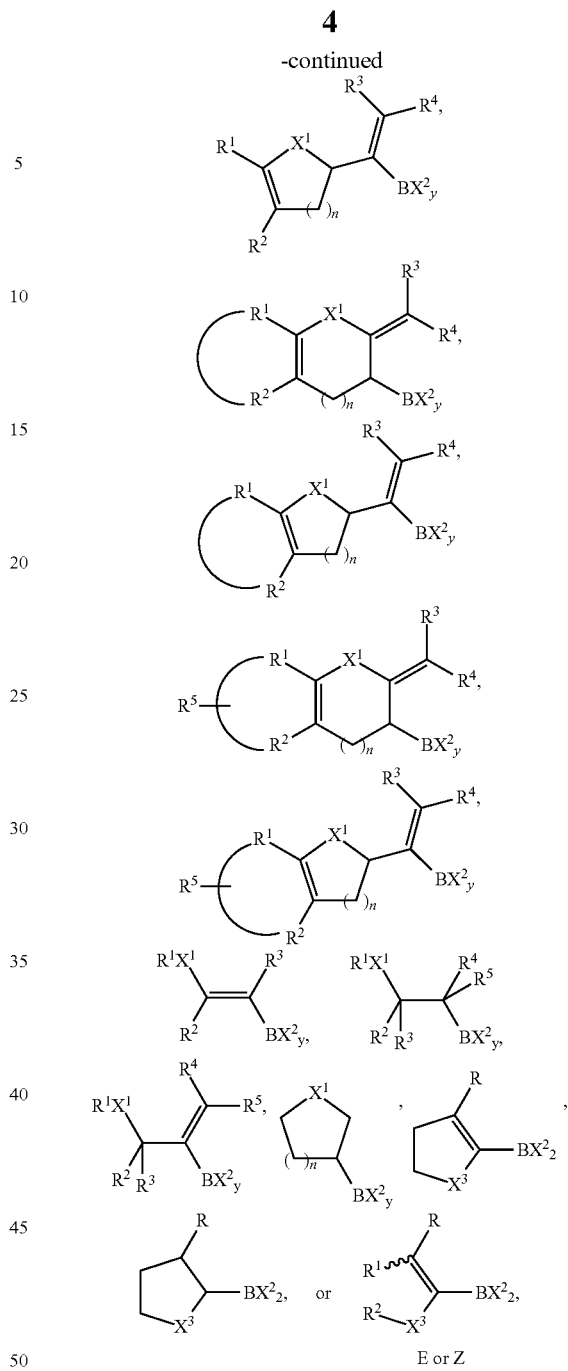

where $X^1$ is O, N, S, or C, where each of R, $R^1$, $R^2$, $R^3$, $R^4$, and $R^5$ are independently selected from: H, a carbonyl functional group, a carbocycle group, a heterocycle, a halide, or an alkyl group, where shown, $R^1$ and $R^2$ together with the carbon atoms they are attached to form a cyclic moiety, wherein $X^2$ is catecholate, pinacolate, ethylene glycolate, 1,3-propanediolate, N-methyliminodiacetate, 2,2'-azanediyldiethanolate, fluoride, or chloride, where n is 0 to 8, and wherein y is from 1 to 3, and where $X^3$ is selected from the group consisting of: C, O, N, and S

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1A illustrates Schemes (1) to (3).
FIG. 1.1B illustrates Schemes (4) to (6).
FIG. 1.1C illustrates Schemes (7) to (9).
FIG. 1.1D illustrates Schemes (10) to (12).
FIG. 1.1E illustrates Schemes (13) to (15).
FIG. 1.1F illustrates Schemes (16) to (18).
FIG. 1.1G illustrates Schemes (19) to (22).
FIG. 1.1H illustrates Schemes (23) to (25).
FIG. 1.2 illustrates embodiments of various organoboron compounds made using embodiments of the present disclosure.
FIG. 1.3 illustrates an embodiment of a reaction scheme to form an organoboron compound.
FIG. 1.4 illustrates an embodiment of a reaction scheme to form an organoboron compound.
FIG. 1.5 illustrates embodiments of a reaction scheme (Scheme 1) to form an organoboron compound and various organoboron compounds. In particular, Scheme 1 shows functionalized benzofuran boronic acid derivatives available through the alkoxyboration reaction. Values represent isolated yields of organotrifluoroborate or MIDA boronate products 4. Values in parentheses represent $^1$H NMR yields of the corresponding catechol boronic ester 3 versus an external mesitylene standard using the ERETIC method (27).
FIG. 2.1(a) and (b) illustrates examples of related B—X bond addition reactivity and an embodiment of a method of the present disclosure.
FIG. 2.2 illustrates a ball and stick figure of an organotrifluoroborate compound.
FIG. 2.3 illustrates an embodiment of various compounds and the corresponding methods.
FIG. 3.1 illustrates an embodiment of a method of making organoboron compounds.

DETAILED DESCRIPTION

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. Different stereochemistry is also possible, such as products of syn or anti addition could be both possible even if only one is drawn in an embodiment.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions:

The term "substituted" refers to any one or more hydrogens on the designated atom (e.g., a carbon atom) that can be replaced with a selection from the indicated group, provided that the designated atom's normal valence is not exceeded, and that the substitution results in a stable compound.

As used herein, "alkyl" or "alkyl group" refers to a branched saturated aliphatic hydrocarbon. Examples of alkyl include, but are not limited to, methyl, ethyl, vinyl, allyl, propyl, butyl, trifluoromethyl, and pentafluoroethyl.

The term "substituted," as in "substituted alkyl", "substituted aryl," "substituted heteroaryl" and the like, means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below, where lower refers to 1 to 6 carbons atoms, for example.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "carbonyl" refers to functional groups such as an amide, ester, ketone, or aldehyde, where each can be substituted or unsubstituted.

The term "carbocycles" refers to a monocyclic or multicyclic ring system of about 5 to about 14 carbon atoms, preferably of about 6 to about 10 carbon atoms. Exemplary carbocycles can refer to functional groups such as phenyl and naphthyl, where each can be substituted or unsubstituted.

The term "heterocycle" is used herein to denote an ring or fused ring structure of carbon atoms with one or more noncarbon atoms, such as oxygen, nitrogen, and sulfur, in the ring or in one or more of the rings in fused ring structures. Preferred examples are furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, carbazole, each which can be substituted or unsubstituted.

General Discussion

Embodiments of the present disclosure provide for methods of making an organoboron compound, organoboron compounds, and the like. An advantage of an exemplary method (e.g., alkoxyboration, aminoboration, or thioboration) of the present disclosure is that organoboron compounds (e.g., organoboron esters) can be made that could not be made previously or the synthesis is much more complicated. In addition, exemplary embodiments of the method can be performed in a few steps in a one-pot synthesis.

In an exemplary embodiment, a method of the synthesis includes the reactions shown in FIG. 1.1A (Schemes 1-3), FIG. 1.1B (Schemes 4-6), FIG. 1.1C (Schemes 7-9), FIG. 1.1D (Schemes 10-12), FIG. 1.1E (Schemes 13-15), FIG. 1.1F (Schemes 16-18), FIG. 1.1G (Schemes 19-22), and FIG. 1.1H (Schemes 23-25).

In an embodiment, $X^1$ can be O, N, S, or C. In an embodiment, $X^1$ can be O, N, or S. In an embodiment, n can be any integer value between 0 and 8, inclusive, or in an embodiment, n can be 2 or 3. In an embodiment, y can be any integer value between 1 and 3, inclusive.

In an embodiment, $X^3$ can be C, O, N, or S. In an embodiment, $X^4$ can be a halogen, trifluoroacetate (TFA), tosylate (OTs), mesylate (OMs), or triflate (OTf). Any and all individual combinations of moieties of $X^3$ and $X^4$ are intended to be covered even if not specifically recited (e.g., $X^3$ is C and $X^4$ is F; $X^3$ is O and $X^4$ is TFA; $X^3$ is S and $X^4$ is OMs; $X^3$ is N and $X^4$ is OTs, and so on).

Schemes (1) to (3) illustrate the formation of the organoboron products where the starting compound includes C=O, C=N, or C=S and the C—C multiple bond is an alkyne.

Schemes (4) to (6) illustrate the formation of the organoboron products where the starting compound includes an alcohol, amine, or a thiol and the C—C multiple bond is an alkyne.

Schemes (7) to (9) illustrate the formation of the organoboron products where the starting compound includes C=O, C=N, or C=S and the C—C multiple bond is an alkene.

Schemes (10) to (12) illustrate the formation of the organoboron products where the starting compound includes an alcohol, amine, or a thiol and the C—C multiple bond is an alkene.

Schemes (13) to (15) illustrate the formation of the organoboron products where the starting compound includes C=O, C=N, or C=S and the C—C multiple bond is an allene.

Schemes (16) to (18) illustrate the formation of the organoboron products where the starting compound includes an alcohol, amine, or a thiol and the C—C multiple bond is an allene.

Schemes (19) to (22) illustrate the formation of the organoboron products through an intermolecular reaction where the starting compound includes an alcohol, amine, or a thiol and the C—C multiple bond is an alkyne, alkene, or allene.

Schemes (23) to (25) illustrate the formation of the organoboron products through an intermolecular reaction where the starting compound includes $X^4$ (a halide or pseudohalide), $X^3$ (any non-hydrogen atom), and the C—C multiple bond is an alkyne or alkene In an embodiment, each of R, $R^1$, $R^2$, $R^3$, $R^4$, and $R^5$, can independently be selected from: H, a carbonyl functional group (substituted or unsubstituted), a carbocycle group (substituted or unsubstituted), a heterocycle (substituted or unsubstituted), a halide (fluoride, chloride, bromide, iodide), and an alkyl group (substituted or unsubstituted). Any and all individual combinations of moieties of R, $R^1$, $R^2$, $R^3$, $R^4$, and $R^5$ are intended to be covered even if not specifically recited (e.g., $R^1$ is a carbonyl functional group, $R^2$ is a hydrogen, $R^3$ is a heterocycle; $R^1$ is a hydrogen, $R^2$ is a carbocycle group, $R^3$ is a heterocycle; $R^1$ is a chloride, $R^2$ is a alkyl group, $R^3$ is a heterocycle; and so on).

In an embodiment, adjacent R groups (e.g., $R^1$, $R^2$, $R^3$, $R^4$, and $R^5$, specifically the pair of $R^1$ and $R^2$, in Scheme 1) together with the carbon atoms they are attached to, can form a cyclic moiety (e.g., C1 to C10, aromatic or non-aromatic). In an embodiment, one or more $R^4$ or $R^5$ moieties, where attached to a cyclic moiety (See, Schemes (3), (6), (9), (12), (15), and (18)), can be attached to the ring, where if more than one $R^4$ or $R^5$ moiety is present, each $R^4$ or $R^5$ moiety can be independently selected. In embodiments having a "curved line" between R1 and R2 (e.g., schemes (2), (3), (5), (6), (8), (9), (11), (12), (14), (15), (17), (18), (23), and (24)), the curved line can represent a carbon chain ($(CH_2)_q$, where q can be 0 to 10). In embodiments having a "curved line" between $X^3$ and $X^4$ (e.g., schemes (23) and (24)), the curved line can represent a carbon chain ($(CH_2)_q$, where q can be 0 to 10) including 0 or more heteroatoms (e.g., $(CH_2)_qO(CH_2)_q$ or $(CH_2)_qNH(CH_2)_q$).

Any and all individual combinations of moieties of R, $R^1$, $R^2$, $R^3$, $R^4$, $R^5$, $X^1$, $X^2$, $X^3$, or $X^4$, are intended to be covered by the structures provided herein even if the specific combination is not recited. Each and every combination of R, $R^1$, $R^2$, $R^3$, $R^4$, $R^5$, $X^1$, $X^2$, $X^3$, and $X^4$ has not been individually provided for sake of clarity.

In an embodiment, the carbonyl functional group can be a moiety selected from: an ester, a ketone, an amide, or an aldehyde, each of which can be substituted or unsubstituted.

In an embodiment, the carbocycle or heterocycle group can be a moiety selected from: phenyl, naphthyl, furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, or carbazole, each of which can be substituted or unsubstituted.

In an embodiment, the alkyl group can be: methyl, ethyl, vinyl, allyl, propyl, butyl, trifluoromethyl, or pentafluoroethyl, each of which can be substituted or unsubstituted.

In an embodiment, $X^2$ can be catecholate, pinacolate, ethylene glycolate, 1,3-propanediolate, N-methyliminodiacetate, 2,2'-azanediyldiethanolate, fluoride, chloride, or similar compounds, each of which can be substituted or unsubstituted.

In an embodiment, the reactant can be reacted with a salt of $BX^2$ and a Lewis acid metal catalyst to form the product, where $X^2$ has the same meaning as described above. In an embodiment, the salt can be an appropriate salt such as an acidic and/or basic salt formed with inorganic and/or organic acids and bases. In an embodiment, the Lewis acid metal catalyst or stoichiometric reagent can be a late transition metal salt, including gold, silver, copper, palladium, or platinum, and the like. In particular, the late transition metal salt can include IPrAuOH, IPrAuCl, IPrAuCl/AgOTf, IPrCuCl/AgTFA, IPrAuCl/AgOTs, IPrAuCl/AgTFA, IPrAuOTf, PEPPSI—IPr/AgOTf, $PdCl_2(PPh_3)_2$/AgOTf, or CuCN*2LiCl.

In an exemplary embodiment, the reactant (e.g., such as those in schemes (1) to (25)) can be first reacted with a base, such as NaH, KH, $CaH_2$, sodium dimsyl, sodium pentadieneide, diethyl zinc, or n-butyllithium or a transmetallation partner such as iPrMgCl in an appropriate solvent, such as toluene, benzene, dichloroethane, dichloromethane, tetrahydrofuran, cyclopentyl methyl ether, tert-butyl methyl ether, diethyl ether, or triethylamine at a temperature in the range of about −78° C. to 50° C. for less than 1 minute to about 30 minutes. Next, the mixture can be reacted with a salt of $BX^2$ at about room temperature for about 10 to 40 minutes. Then the mixture can be reacted with a Lewis acid metal catalyst or stoichiometric reagent at a temperature of about 25° C. to 110° C. for about 1 to 18 hours. In some instances, a promoter, such as the sodium, potassium, lithium, and silver salts of trifluoroacetic acid, p-toluenesulfonic acid, triflic acid, bis(trifluoromethane)sulfonimide, hexafluoroantimonic acid, hexafluorophosphoric acid, or tetrafluoroboric acid, may also be used. The order of the steps and the order of the addition of additives, promoters, catalysts, and stoichiometric reagents can be adjusted or changed so long as the products are still produced. In an embodiment, the conversion can be greater than 90% or 95%.

In an embodiment, the amount of Lewis acid metal catalyst used can be less than about 1 mol % to about 25 mol % or about 5 mol % to about 10 mol %. The amount of a stoichiometric Lewis acid metal reagent can be less than 30 mol % to about 100 mol % The concentrations of the components can be adjusted accordingly depending upon the reactants, products, temperature, pH, reaction time, and the like. Example 1 illustrates an exemplary method and compounds formed using an embodiment of the method.

In an embodiment, the organoboron compound can be represented by the following structures:

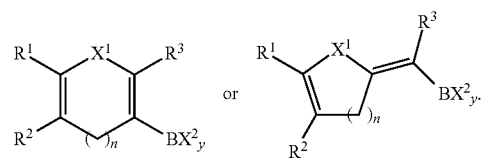

In an embodiment, $X^1$, $X^2$, $R^1$, $R^2$, $R^3$, n, and y can have the same meaning as described above in reference to the method of making an organoboron compound. In an embodiment, each combination of moieties and variables (e.g., $X^1$, $X^2$, $R^1$, $R^2$, $R^3$, n, and y) are intended to be included herein.

In an embodiment, the organoboron compound can be represented by the following structures:

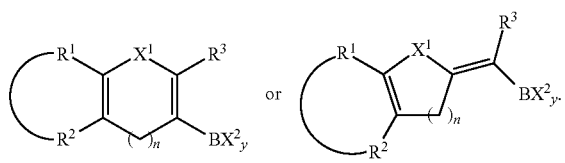

In an embodiment, $X^1$, $X^2$, $R^1$, $R^2$, $R^3$, n, and y can have the same meaning as described above in reference to the method of making an organoboron compound. In an embodiment, each combination of moieties and variables (e.g., $X^1$, $X^2$, $R^1$, $R^2$, $R^3$, n, and y) are intended to be included herein.

In an embodiment, the organoboron compound can be represented by the following structures:

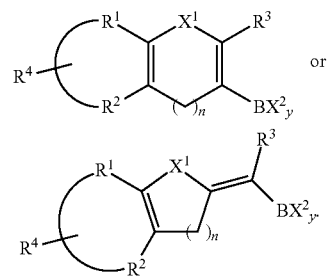

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, n, and y) are intended to be included herein.

In an embodiment, the organoboron compound can be represented by the following structures:

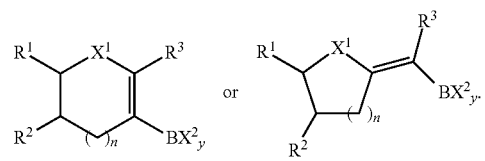

In an embodiment, $X^1$, $X^2$, $R^1$, $R^2$, $R^3$, n, and y can have the same meaning as described above in reference to the method of making an organoboron compound. In an embodiment, each combination of moieties and variables (e.g., $X^1$, $X^2$, $R^1$, $R^2$, $R^3$, n, and y) are intended to be included herein.

In an embodiment, the organoboron compound can be represented by the following structures:

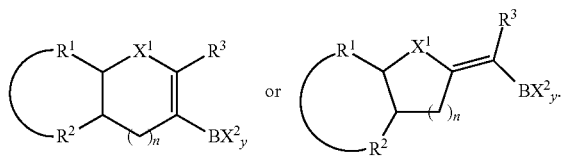

In an embodiment, $X^1$, $X^2$, $R^1$, $R^2$, $R^3$, n, and y can have the same meaning as described above in reference to the method of making an organoboron compound. In an embodiment, each combination of moieties and variables (e.g., $X^1$, $X^2$, $R^1$, $R^2$, $R^3$, n, and y) are intended to be included herein.

In an embodiment, the organoboron compound can be represented by the following structures:

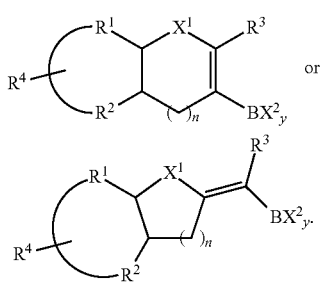

In an embodiment, $X^1$, $X^2$, $R^1$, $R^2$, $R^3$, $R^4$, n, and y can have the same meaning as described above in reference to the method of making a organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

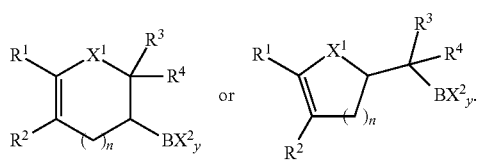

In an embodiment, $X^1$, $X^2$, $R^1$, $R^2$, $R^3$, $R^4$, n, and y can have the same meaning as described above in reference to the method of making a organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

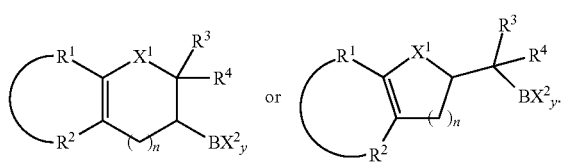

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, n, and y) are intended to be included herein.

In an embodiment, the organoboron compound can be represented by the following structures:

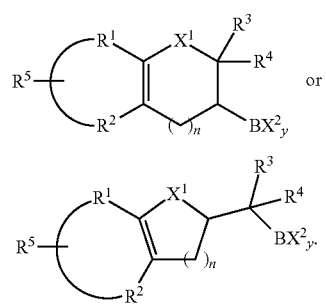

In an embodiment, $X^1$, $X^2$, $R^1$, $R^2$, $R^3$, $R^4$, $R^5$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, $R^5$, n, and y) are intended to be included herein.

In an embodiment, the organoboron compound can be represented by the following structures:

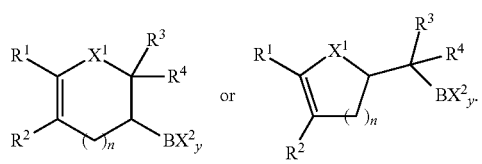

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

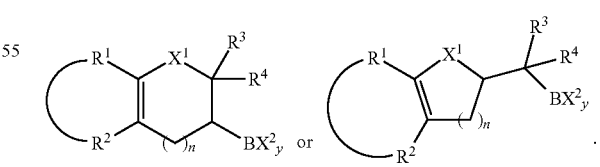

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

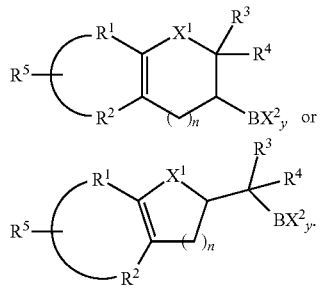

In an embodiment, $X^1$, $X^2$, $R^1$, $R^2$, $R^3$, $R^4$, $R^5$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, $R^5$, n, and y) are intended to be included herein.

In an embodiment, the organoboron compound can be represented by the following structures:

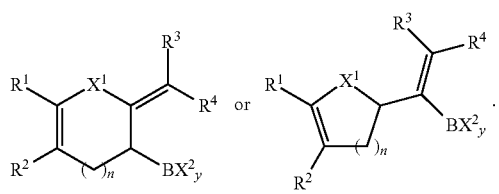

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

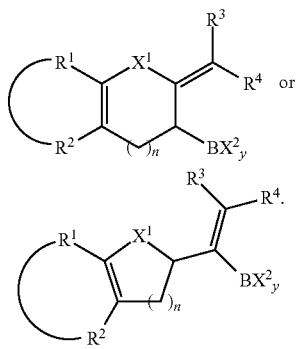

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

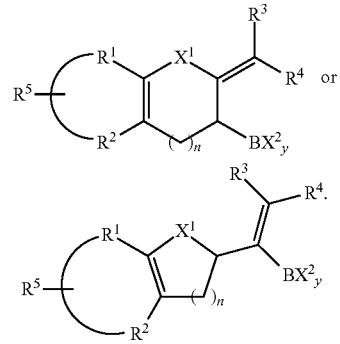

In an embodiment, $X^1$, $X^2$, $R^1$, $R^2$, $R^3$, $R^4$, $R^5$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, $R^5$, n, and y) are intended to be included herein.

In an embodiment, the organoboron compound can be represented by the following structures:

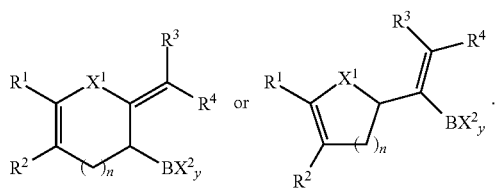

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

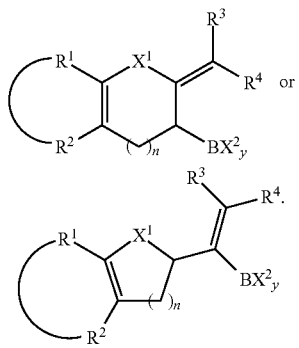

In an embodiment, $X^1$, $X^2$, $R^1$, $R^2$, $R^3$, $R^4$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, n, and y) are intended to be included herein.

In an embodiment, the organoboron compound can be represented by the following structures:

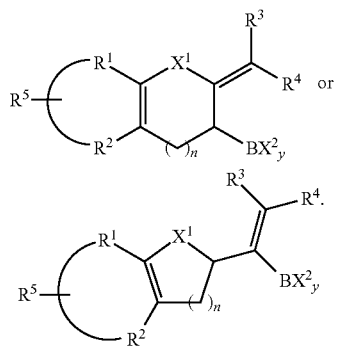

In an embodiment, $X^1$, $X^2$, $R^1$, $R^2$, $R^3$, $R^4$, $R^5$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, $R^5$, n, and y) are intended to be included herein.

In an embodiment, the organoboron compound can be represented by the following structure

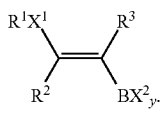

In an embodiment, $X^1$, $X^2$, $R^1$, $R^2$, $R^3$, n, and y can have the same meaning as described above in reference to the method of making an organoboron compound. In an embodiment, each combination of moieties and variables (e.g., $X^1$, $X^2$, $R^1$, $R^2$, $R^3$, n, and y) are intended to be included herein.

In an embodiment, the organoboron compound can be represented by the following structure:

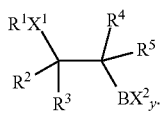

In an embodiment, $X^1$, $X^2$, $R^1$, $R^2$, $R^3$, $R^4$, $R^5$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, $R^5$, n, and y) are intended to be included herein.

In an embodiment, the organoboron compound can be represented by the following structure:

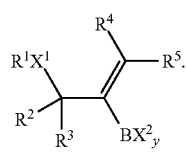

In an embodiment, $X^1$, $X^2$, $R^1$, $R^2$, $R^3$, $R^4$, $R^5$, n, and y can have the same meaning as described above in reference to the method of making an organoboron compound. In an embodiment, each combination of moieties and variables (e.g., $X^1$, $X^2$, $R^1$, $R^2$, $R^3$, $R^4$, $R^5$, n, and y) are intended to be included herein.

In an embodiment, the organoboron compound can be represented by the following structure:

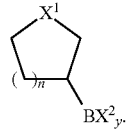

In an embodiment, $X^1$, $X^2$, n, and y can have the same meaning as described above in reference to the method of making an organoboron compound. In an embodiment, each combination of moieties and variables (e.g., $X^1$, $X^2$, n, and y) are intended to be included herein.

In an embodiment, the organoboron compound can be represented by the following structure:

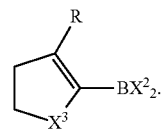

In an embodiment, R, $X^3$, and $X^2$, can have the same meaning as described above in reference to the method of making an organoboron compound. In an embodiment, each combination of moieties and variables (e.g., R, $X^3$, and $X^2$) are intended to be included herein.

In an embodiment, the organoboron compound can be represented by the following structure:

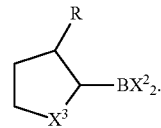

In an embodiment, R, $X^3$, and $X^2$, can have the same meaning as described above in reference to the method of making an organoboron compound. In an embodiment, each combination of moieties and variables (e.g., R, $X^3$, and $X^2$) are intended to be included herein.

In an embodiment, the organoboron compound can be represented by the following structure:

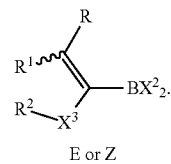

E or Z

In an embodiment, R, $R^1$, $R^2$, $R^3$, $X^3$, and $X^2$, can have the same meaning as described above in reference to the method of making an organoboron compound. In an embodiment, each combination of moieties and variables (e.g., R, $R^1$, $R^2$, $R^3$, $X^3$, and $X^2$) are intended to be included herein.

FIG. 1.2 illustrates embodiments of various organoboron compounds made using embodiments of the present disclosure.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction:

A method for the intramolecular anti addition of boron-oxygen bonds across alkynes is disclosed. This alkoxyboration reaction is conducted as a one-pot sequence starting from 2-alkynylphenols and generates 3-benzofuranyl boronic esters inaccessible using other borylation methods. The products are isolated as the corresponding trifluoroborate salts or MIDA boronate for synthetic ease.

Discussion:

We have developed an alkoxyboration reaction of alkynes to simultaneously install new C—O and C—B bonds from the easily generated B—O bonds of boric esters (such as A). This new reactivity is compatible with a wide variety of functional groups sensitive to other borylation methods and provides access to new bench-stable organotrifluoroborate or MIDA boronate coupling partners.

We envisioned that an intramolecular anti-alkoxyboration reaction could be promoted by a Lewis acidic metal catalyst. A variety of metal catalysts were examined for competence in converting boric ester A into boronic ester B (Table 1). In the absence of catalyst, no conversion of boric ester n was observed (entry 1). The N-heterocyclic carbene gold complexes IPrAuOH and IPrAuCl (entries 2 and 3) gave unreacted boric ester A. However, IPrAuCl with a variety of silver salt activators afforded the desired alkoxyboration catalyst in high conversion (entries 4-6). Identical reactivity was observed with authentic IPrAuOTf, eliminating the possibility of a "silver effect" (entry 7). Interestingly, other commonly used late transition metal complexes were found to be ineffective as alkoxyboration catalysts (entries 8-10).

TABLE 1

Optimization of alkoxyboration metal catalyst.

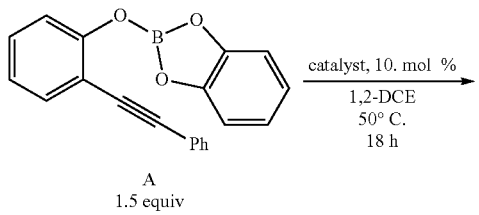 [SMILES: C(#Cc1ccccc1OB1Oc2ccccc2O1)c1ccccc1]

A
1.5 equiv catalyst, 10. mol %
1,2-DCE
50° C.
18 h

TABLE 1-continued

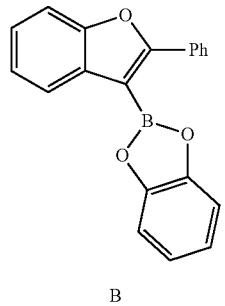

B

| Entry | Catalyst | Conversion[b] (B:A) |
|---|---|---|
| 1 | None | only A |
| 2 | IPrAuOH | only A |
| 3 | IPrAuCl | only A |
| 4 | IPrAuCl/AgOTf | >95:5 |
| 5 | IPrAuCl/AgOTs | >95:5 |
| 6 | IPrAuCl/AgTFA | >95:5 |
| 7 | IPrAuOTf | >95:5 |
| 8 | PEPPSI-IPr/AgOTf[c,d] | only A |
| 9 | PdCl$_2$(PPh$_3$)$_2$/AgOTf[c,d] | only A |
| 10 | IPrCuCl/AgTFA | only A |

IPr = 1,3-bis(2,6-diisopropylphenyl)-1,3-dihydro-2H-imidazol-2-ylidene
[a]Conditions: 0.10M A in 1,2-dichloroethane.
[b]Determined by $^1$H and $^{11}$B NMR spectroscopy.
[c]Using 20. mol % AgOTf.
[d]Reaction time, 6 h.

Further optimization of the reaction conditions resulted in a one-pot procedure starting from 2-alkynyl phenols (Scheme 1 as shown in FIG. 1.3). Following deprotonation of substrate C by NaH, the boric ester moiety was installed by electrophilic trapping using B-chlorocatecholborane, a commercially available reagent used in the deprotection of MOM-protected alcohols. Heating intermediate A in the presence of catalytic IPrAuCl/NaTFA afforded the desired alkoxyboration product B in high conversion. In this one-pot procedure, NaTFA was used as an activator instead of the silver salts shown in Table 1 due to its tolerance of the equivalent of NaCl present after installation of the boric ester in step 2.

Isolation of alkoxyboration product B proved to be challenging. The electron-rich nature of the 3-benzofuranyl system renders the C—B bond sensitive to protonolysis by atmospheric moisture. We therefore sought to isolate alkoxyboration product B as the corresponding MIDA boronate or trifluoroborate salt, both of which are air-stable indefinitely. Treatment of a microscale alkoxyboration reaction mixture with N-methyliminodiacetic acid (H$_2$MIDA) allowed for isolation of the desired product in 46% yield (Scheme 2 as shown in FIG. 1.4) with the protodeboronated product as the mass balance. Alternatively, treatment of the alkoxyboration reaction mixture with KHF$_2$ afforded the benzofuranyl trifluoroborate salt in 47% yield. For synthetic ease and optimal yields, we therefore opted to isolate the catechol boronic ester alkoxyboration products as the corresponding trifluoroborate salts.

With optimized reaction and isolation conditions in hand, we set out to explore the substrate scope of this alkoxyboration reaction (FIG. 1.5).

Simple aryl and alkyl substitution at the benzofuran 2-position is tolerated with high yield (a). The reaction is regioselective when using a diethynylphenol to afford alkyne-substituted benzofuran b. Unlike traditional metalation/electrophilic trapping methods of generating boronic esters, the alkoxyboration reaction is compatible with a variety of reactive functional groups, such as aryl halides (c, j), silyl ethers (d), free alcohols (e, n), amides (m, n), esters (f, g, i, k, and l), nitriles (j), protected amino acids (O), and aldehydes (h), and is expected to be compatible with ketones (nl). The high degree of functionality available in the alkoxyboration products provides many functional group handles for subsequent transformations.

Example 2

Brief Introduction

Despite nearly 70 years of research into the addition of B—X σ bonds to C—C multiple bonds, a method for B—O bond activation has not yet been reported. Such a transformation could allow for the synthesis of versatile oxygen-containing organoboron reagents for organic synthesis. We herein report the realization of an alkoxyboration reaction, adding B—O σ bonds to alkynes. O-Heterocyclic boronic acid derivatives can be produced using this transformation, which is mild and exhibits broad functional group compatibility.

Discussion:

Boronic acids and their derivatives are versatile reagents in modern organic synthesis, and the hydroboration reaction is a well-established method for generating these building blocks through the addition of B—H bonds across C—C multiple bonds (1). First described by Hurd in 1948 (2) and later developed in detail by Brown (3), this reaction has inspired many catalyzed variants (4, 5). Recently, several compelling examples of related B—X bond addition reactivity have been reported for X=C (6, 7), Si (8, 9), Sn (10), and S (11) (FIG. 2.1.a). These transformations generally proceed through the oxidative addition of a catalytic transition metal such Ni(0), Pd(0), or Pt(0) into the B—X σ bond.

Despite this progress, the corresponding activation of B—O bonds and addition to C—C multiple bonds-alkyoxyboration—has remained elusive for 65 years (12,13). This striking dearth of B—O bond activation reactivity may be due to the high strength of the B—O bond (14), rendering it unreactive towards oxidative addition and thus preventing the successful application of Ni, Pd, or Pt catalysis (6-11). Given that ethers are found in many diverse classes of natural products (15) and in nearly 25% of the top-grossing pharmaceuticals in the United States for 2012 (16), the development of an alkoxyboration reaction could allow for the preparation of oxygen-containing building blocks useful in drug discovery and materials science (16,17).

Herein we report the realization of an alkoxyboration reaction of alkynes, through which new O-heterocyclic organoboronate coupling partners are available for downstream functionalization. The high functional-group tolerance of this reaction enables downstream divergent synthesis of functionalized benzofurans—the ability to accesses multiple benzofurans from one bench stable precursor. In contrast, current methods for synthesizing benzofurans often rely on harsh conditions that limit compatibility with functional groups desirable for divergent synthesis (18).

We envisioned that the desired alkoxyboration reactivity could be promoted through an activation pathway employing a bifunctional Lewis acidic/Lewis basic catalyst, which could simultaneously activate both the alkyne and the B—O σ bond partners. We anticipated that this unique strategy could allow for the anti addition of B—O bonds across alkynes by circumventing the previous problematic strategy of oxidative cleavage of the B—O bond.

Our optimized one-pot procedure begins with 2-alkynyl phenols (1), which are converted into the requisite boric ester intermediate 2 using the readily available reagent B-chlorocatecholborane (Scheme 1, FIG. 1.5). Treatment of this intermediate with the commercially available Lewis acidic gold(I) precatalyst IPrAuCl and NaTFA affords alkoxyboration product 3 in good to excellent conversion. Interestingly, our examination of alternative π-Lewis acidic transition metal catalysts revealed no other active catalysts aside from Au(I) (19). For synthetic ease, the catechol boronic ester alkoxyboration product 3 was converted into either the organotrifluoroborate (20) or N-methyliminodiacetic acid (MIDA) boronate (21) derivative, 4, both of which are air stable indefinitely.

Organotrifluoroborate 4a is readily isolated in high yield using a chromatography-free purification, making this derivatization method particularly amenable to applying the alkoxyboration reaction on preparative scale (FIG. 2.2). The corresponding MIDA derivative (4b) provides an option for purification by silica gel chromatography, but this comes at the cost of slightly diminished yield. Single-crystal X-ray diffraction analysis of 4b allowed for the unambiguous identification of the alkoxyboration product.

The alkoxyboration reaction is tolerant of a variety of functional groups suitable for downstream reactivity. Aryl bromide 4c, silyl-protected alcohol 4d, terminal alkyne 4f, amide 4g, esters 4h and 4i, and the functionally-dense iodonitrile 4j are compatible with the reaction conditions. Many of these alkoxyboration reactions proceed smoothly at 50° C., although the reactions generating 4d, 4g, 4h, and 4j required heating to 90° C. in order to affect full conversion. We attribute the relatively slow formation of 4d to the high steric encumbrance from the silyl ether at the 2-position of the benzofuran. The cyclization of substrates containing Lewis basic nitrogen atoms (forming 4g, 4h, and 4j) was likely retarded by reversible N—B coordination that was observed by $^{11}$B nuclear magnetic resonance (NMR) spectroscopy.

Notably, many of these products contain functional groups incompatible with commonly employed methods of benzofuran synthesis (18), including via other borylation techniques (FIG. 2.3). In one frequently used borylation technique, an aryl lithium intermediate is trapped by a boron electrophile (Method 1); thus electrophiles such as carbonyl or nitrile groups and enolizable protons are not generally tolerated due to the highly nucleophilic and basic nature of the requisite organolithium intermediate (22). Aryl halides may also suffer from undesired lithium/halogen exchange. The Miyaura borylation is a more mild alternative that is compatible with electrophilic functional groups (Method 2), but aryl halides are not tolerated because this reaction is catalyzed by Pd(0), which also activates aryl halide bonds (23). Finally, the Ir-catalyzed C—H activation/borylation reaction is an effective means of accessing aryl boronic acid derivatives through C—H activation (Method 3), but this reaction is regioselective for either 2- or 7-borylation; 3-borylated benzofurans such as those available through the alkoxyboration reaction cannot be synthesized regioselectively through C—H activation/borylation (24).

We set out to demonstrate the utility in divergent synthesis of the alkoxyboration products enabled through this synthesis in subsequent functionalization steps. Rh-catalyzed conjugate addition of 4a into methyl vinyl ketone using the method developed by Batey (25) provides β-benzofuranyl ketone 6 in moderate yield (eq 1). Organotrifluoroborate 4i was subjected to Suzuki-Miyaura coupling conditions described by Molander and Biolatto (26) to afford the cross-coupled product 3-arylated benzofuran 8 with concomitant methanolysis of the ethyl ester (eq 2). These two transformations suggest the potential for broad applicability of these functionalized alkoxyboration products in a variety of C—C bond-forming reactions.

clic boronic acid derivatives sufficient for multistep synthesis may be prepared using the alkoxyboration method.

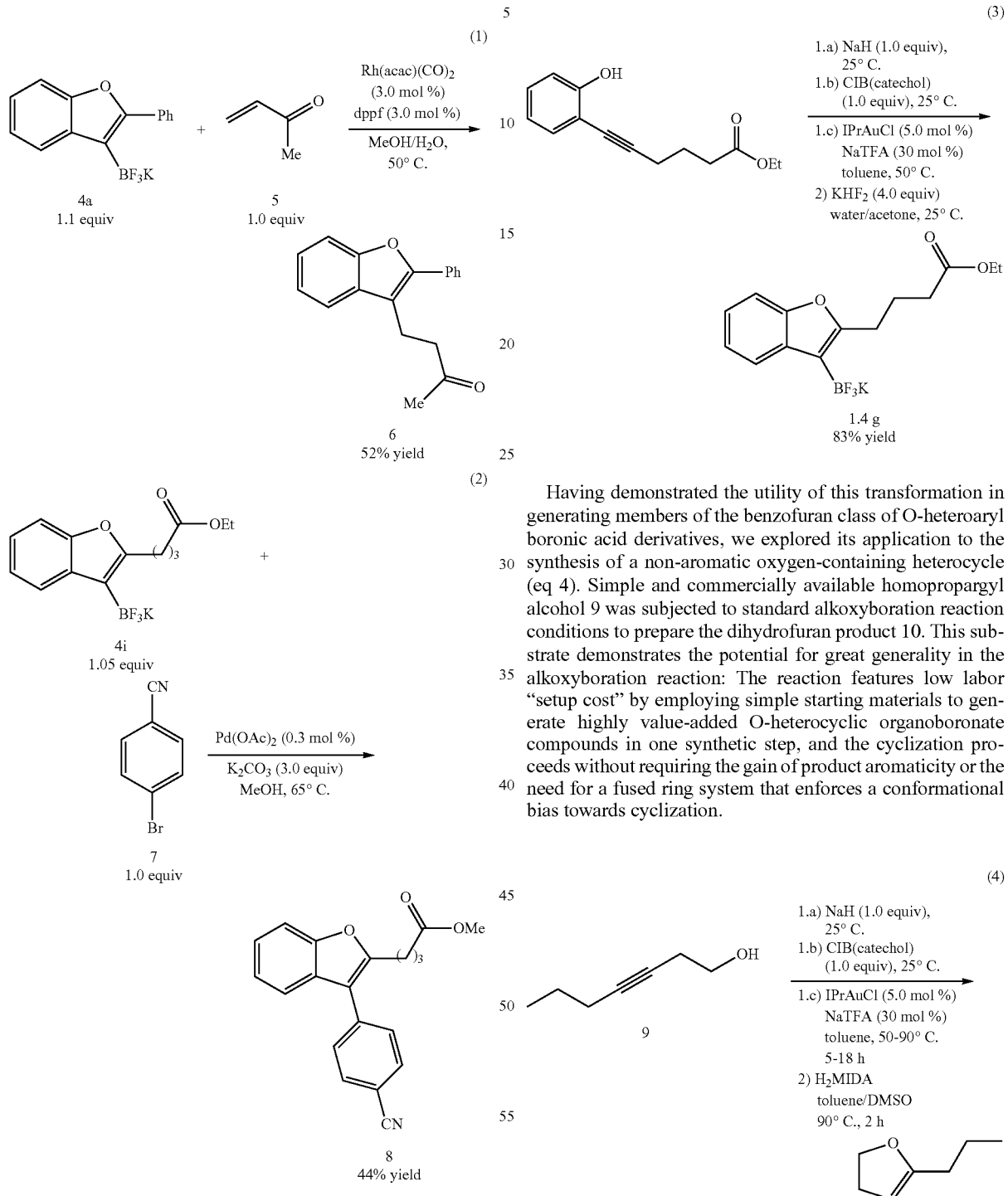

Having demonstrated the utility of this transformation in generating members of the benzofuran class of O-heteroaryl boronic acid derivatives, we explored its application to the synthesis of a non-aromatic oxygen-containing heterocycle (eq 4). Simple and commercially available homopropargyl alcohol 9 was subjected to standard alkoxyboration reaction conditions to prepare the dihydrofuran product 10. This substrate demonstrates the potential for great generality in the alkoxyboration reaction: The reaction features low labor "setup cost" by employing simple starting materials to generate highly value-added O-heterocyclic organoboronate compounds in one synthetic step, and the cyclization proceeds without requiring the gain of product aromaticity or the need for a fused ring system that enforces a conformational bias towards cyclization.

We next explored the scalability of the alkoxyboration reaction and tolerance of lower catalyst loading. Bromide-containing phenol 1c was successfully converted to more than 1 g of MIDA boronate 4c on a 5.1 mmol scale with 2.0% gold catalyst (eq 3). Full conversion of starting material was affected even with a lower Au catalyst loading. This convenient scalability demonstrates that quantities of O-heterocy- In accordance with our strategy for bifunctional Lewis acidic/Lewis basic substrate activation, we propose the catalytic cycle shown in Scheme 2. The bifunctional catalyst IPrAuTFA can be generated in situ from IPrAuCl and NaTFA. Reaction of the Lewis basic trifluoroacetate moiety with electrophilic boric ester 2a gives nucleophilic boronate 12. The resulting Lewis acidic Au(I) cation may then bind to the alkyne (13), increasing its electrophilicity. Nucleophilic attack on the alkyne-Au π complex by the phenol B—O bond often proceed through oxidative addition of a low-valent metal catalyst into the B—X bond. We believe that the new activation strategy employed in the alkoxyboration reaction could be extended to other types of B—X bonds in order to provide additional reactivity complementary to preexisting methods.

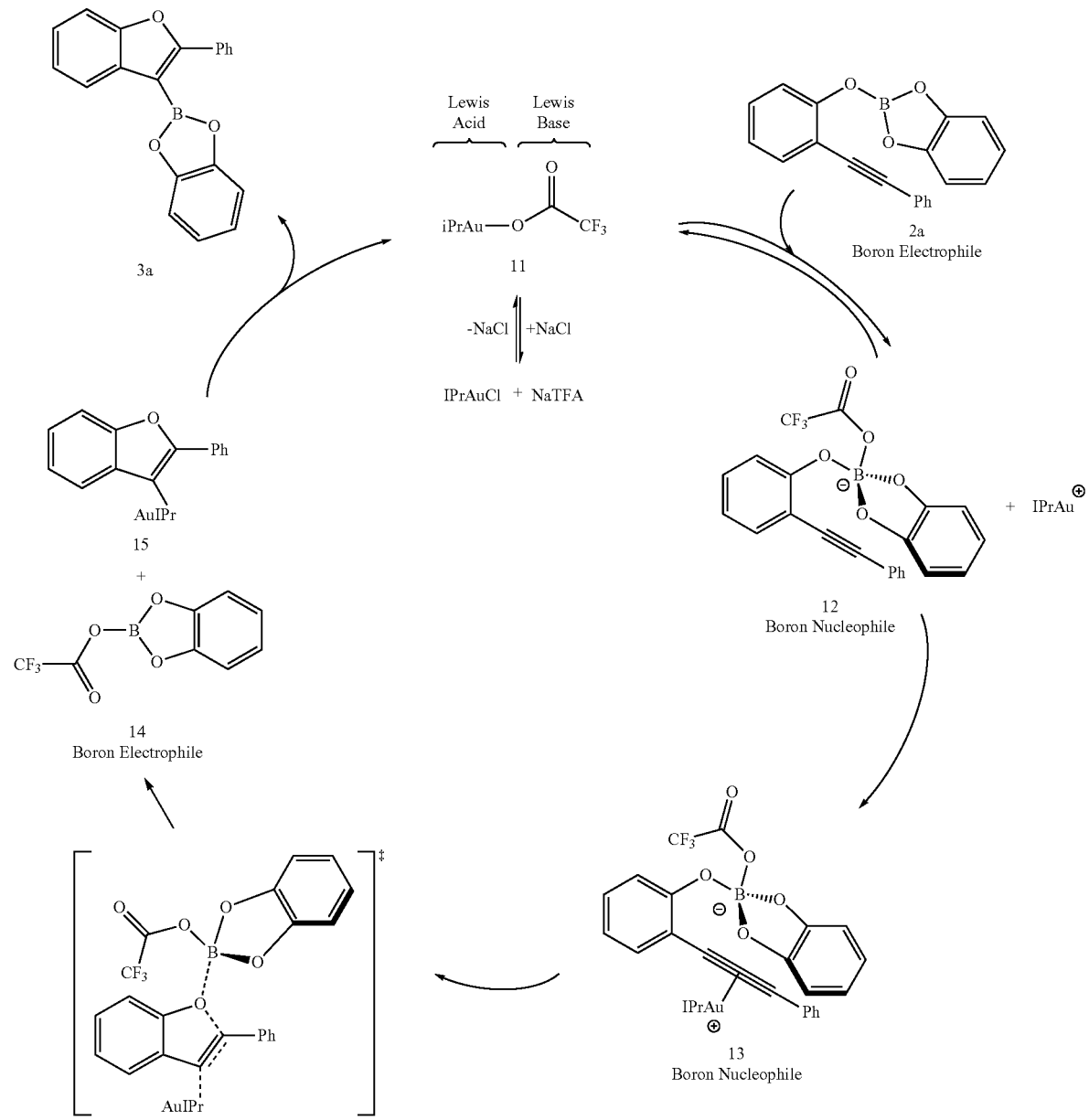

Scheme 2. Mechanistic hypothesis featuring the bifunctional Lewis acidic/Lewis basic catalyst IPrAuTFA.

would provide neutral intermediates: boron electrophile 14 and organogold nucleophile 15, which could recombine to regenerate 11 with concomitant formation of the observed alkoxyboration product 3a. Thus, the IPrAu⁺ moiety of the catalyst activates the alkyne for nucleophilic attack, and the TFA counterion allows for reversible tuning at boron from electrophilic to nucleophilic. This reaction manifold is fundamentally unique from the metal-catalyzed addition of B—C, B—Si, B—Sn, and B—S addition reactions, which This alkoxyboration reaction proceeds through an unprecedented B—O bond activation. This fundamentally new activation is showcased in a mild, scalable technique for the preparation of O-heterocyclic boronic acid derivatives and downstream functionalized benzofurans. The reaction provides a simple new bond disconnection for constructing these motifs with different regioselectivity and broader functional group compatibility than existing methods. This compatibility yields highly functionalized bench-stable cross-coupling and Michael addition partners for divergent synthesis that are not directly accessible using alternative methods.

References

1. D. G. Hall, *Boronic Acids: Preparation and Applications in Organic Synthesis, Medicine, and Materials* (Wiley-VCH, Weinheim, Germany, 2011).
2. D. T. Hurd, *J. Am. Chem. Soc.* 70, 2053-2055 (1948).
3. H. C. Brown, *Tetrahedron* 12, 117-138 (1961).
4. D. Männig, H. Nöth, *Angew. Chem. Int. Ed. Engl.* 24 878-879 (1985).
5. A.-M. Carrol, T. P. O'Sullivan, P. J. Guiry, *Adv. Synth. Catal.* 347, 609-631, (2005).
6. M. Suginome, A. Yamamoto, M. Murakami, *J. Am. Chem. Soc.* 125, 6358-6359 (2003).
7. M. Suginome, M. Shirakura, A. Yamamoto, *J. Am. Chem. Soc.* 128, 14438-14439 (2009).
8. M. Suginome, H. Nakamura, Y. Ito, *Chem. Commun.* 2777-2778 (1996).
9. M. Suginome, H. Nakamura, Y. Ito, *Angew. Chem. Int. Ed. Engl.* 36, 2516-2518 (1997).
10. S. Onozawa, Y. Hatanaka, T. Sakakura, S. Shimada, M. Tanaka, *Organometallics* 15, 5450-5452 (1996).
11. T. Ishiyama, K. Nishijima, N. Miyaura, A. Suzuki, *J. Am. Chem. Soc.* 115, 7219-7225 (1993).
12. C—N bonds, see: R. H. Cragg, M. F. Lappert, B. P. Tilley, *J. Chem. Soc.* 2108-2115 (1964).
13. N. Matsumi, Y. Chujo, *Macromolecules* 31, 3802-3806 (1998).
14. R. T. Sanderson, *Polar Covalence* (Academic Press, Waltham, Mass., U.S., 1983).
15. P. Dominguez de Maria, R. W. van Gemert, A. J. J. Straathof, U. Hanefeld, *Nat. Prod. Rep.* 27, 370-392 (2010).
16. Drugs.com, U.S. *Pharmaceutical Sales*-2012 (http://www.drugs.com/stats/top100/2012/sales).
17. S. Anderson, P. N. Taylor, G. L. B. Verschoor, *Chem. Eur. J.* 10, 518-527 (2004).
18. J. A. Joule, K. Mills, *Heterocyclic Chemistry*, 5$^{th}$ Ed. (Chichester, United Kingdom, 2010).
19. Materials, methods, and X-ray diffraction details are available as supplementary materials on *Science Online*.
20. G. A. Molander, N. Ellis, *Acc. Chem. Res.* 40, 275-286 (2007).
21. E. P. Gillis, M. D. Burke, *J. Am. Chem. Soc.* 130, 14084-14085 (2008).
22. A. Nagaki, Y. Moriwaki, J. Yoshida, *Chem. Commun.* 48, 11211-11213 (2012).
23. T. Ishiyama, M. Murata, N. Miyaura, *J. Org. Chem.* 60, 7508-7510 (1995).
24.1. A. I. Mkhalid, J. H. Barnard, T. B. Marder, J. M. Murphy, J. F. Hartwig, *Chem. Rev.* 110, 890-931 (2010).
25. R. A. Batey, A. N. Thadani, D. V. Smil, *Org. Lett.* 1, 1683-1686 (1999).
26. G. A. Molander, B. Biolatto, *J. Org. Chem.* 68, 4302-4314 (2003).
27. S. Akoka, L. Barantin, M. Trierweiler, *Anal. Chem.* 71 2554-2557 (1999).

Example 3

FIG. 3.1 illustrates an embodiment of forming a boronic compound. The aryl bromide starting material is converted to the corresponding Grignard reagent through a magnesium/halogen exchange reaction. Treatment with a stoichiometric copper reagent, such as CuCN.2LiCl, promotes anti addition across the tethered alkyne to form a 2-metallated indole. Trapping of this organocopper nucleophile with an electrophilic boron reagent or other boron transmetalation reagent such as B-chlorocatecholborane, B-chloropinacolborane, or B-trifluoroacetocatecholborane is expected to provide the 2-borylated indole shown (product shown for trapping with B-chlorocatecholborane), which could be converted to the corresponding organotrifluoroborate or MIDA boronate derivative. Thus, this method provides selective borylation at the 2 position of the new heterocyclic ring in a manner complementary to the 3-selective borylations shown in FIGS. 1.1A-2.3.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A method of making an organoboron compound, comprising a reaction described by one of the following schemes:

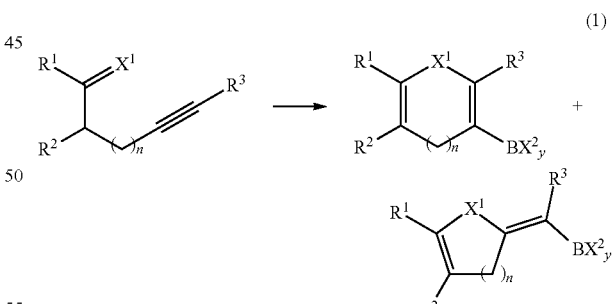

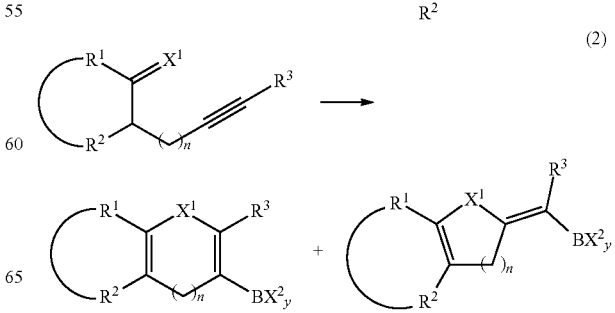

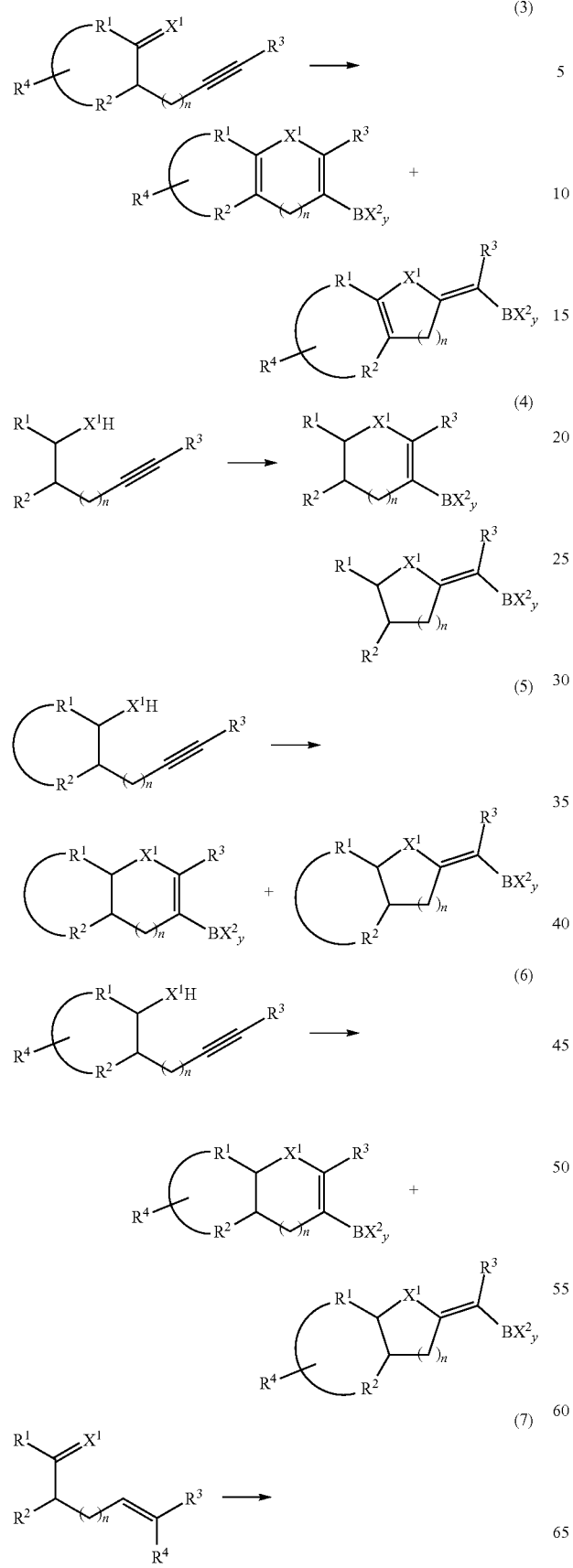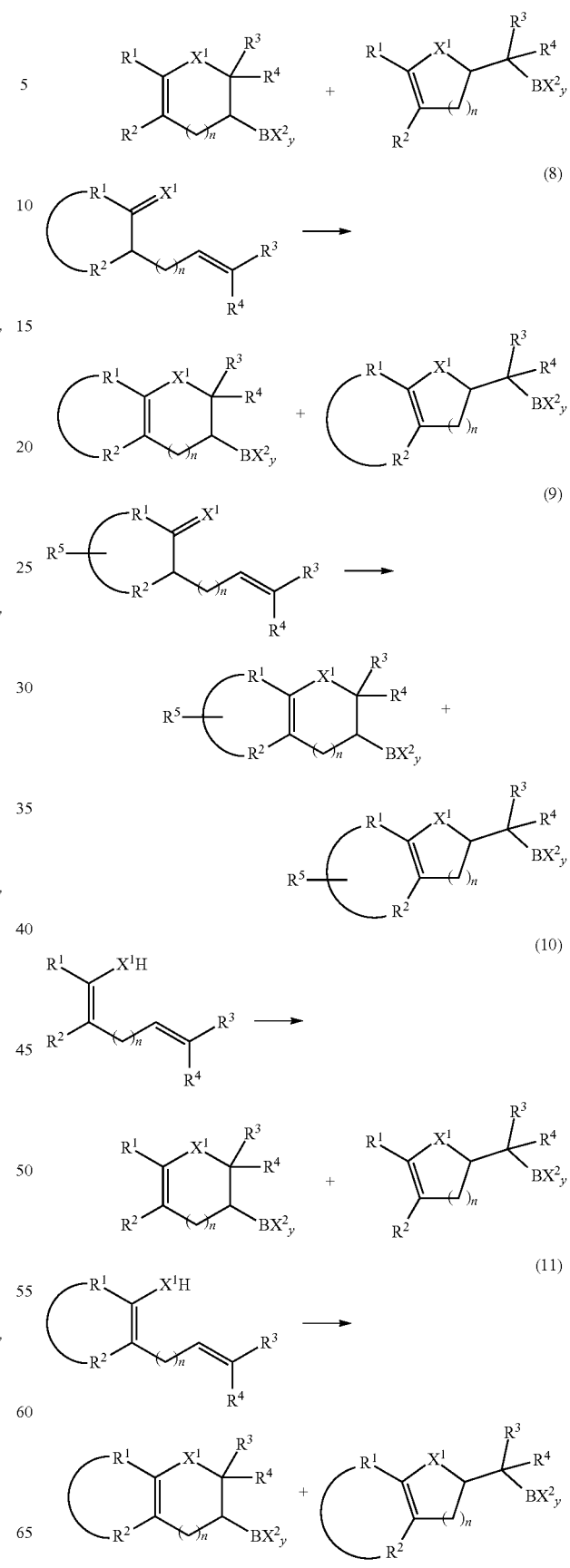

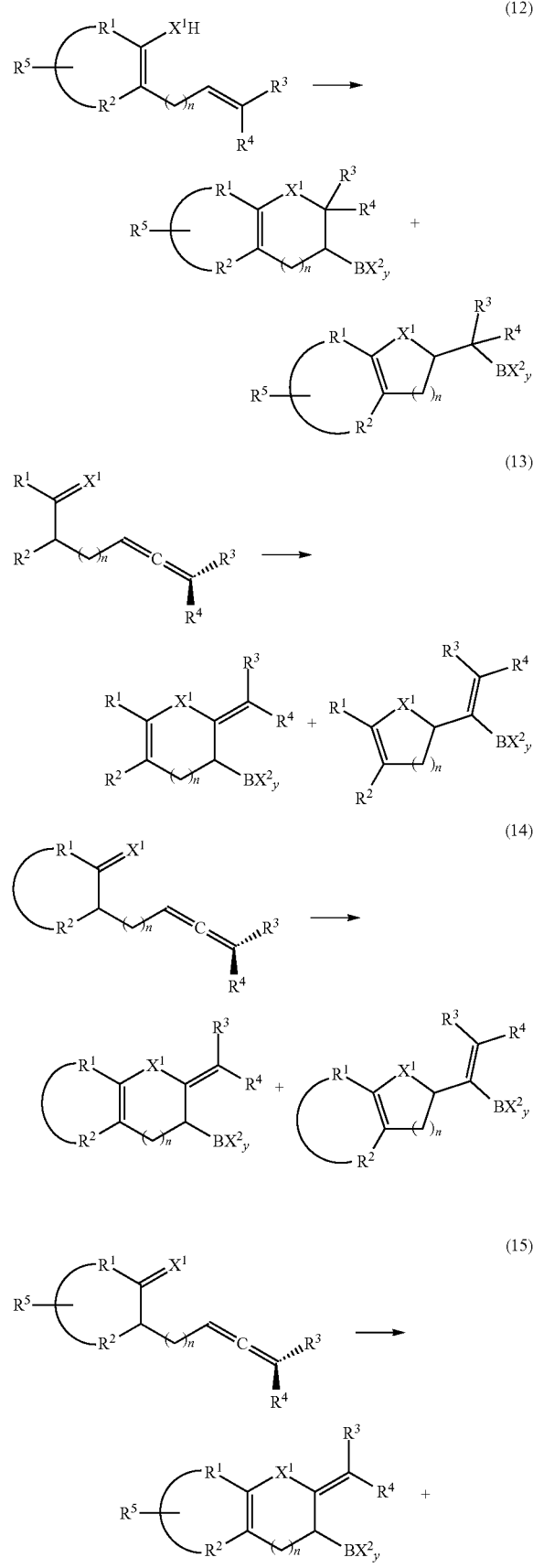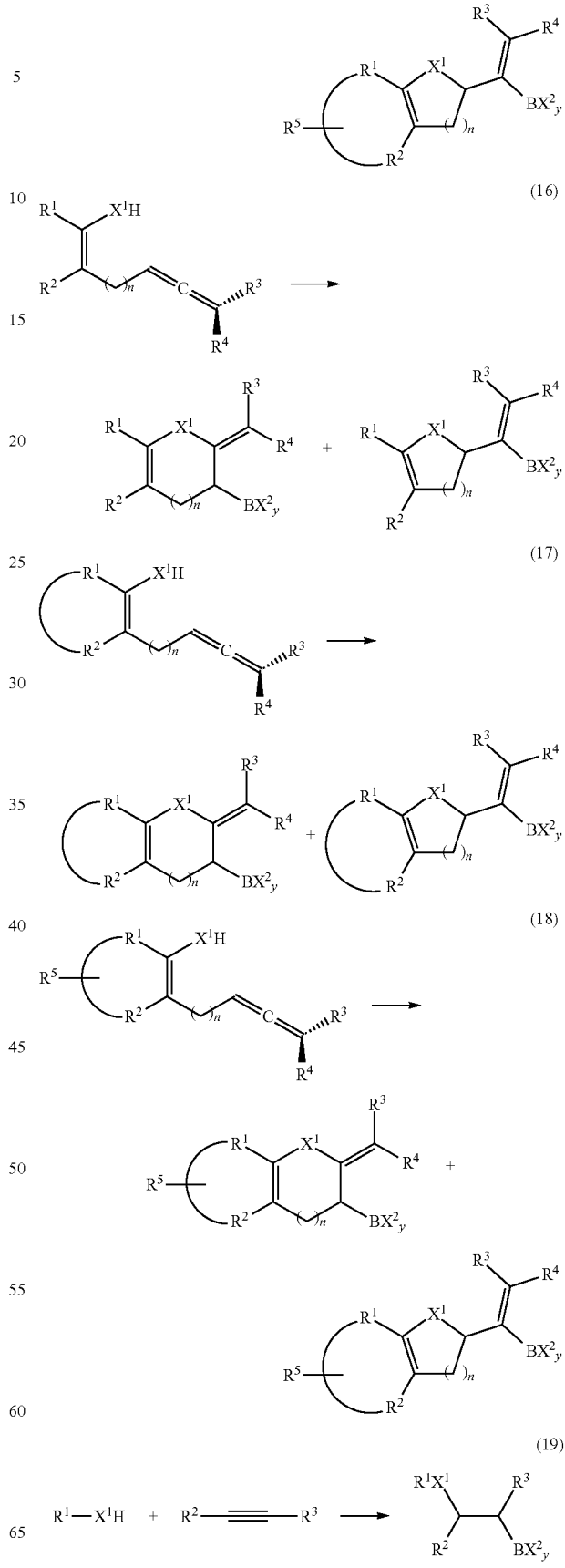

-continued

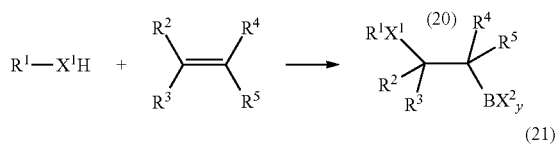

(20)

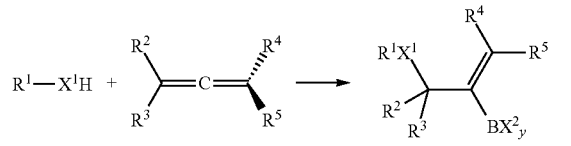

(21)

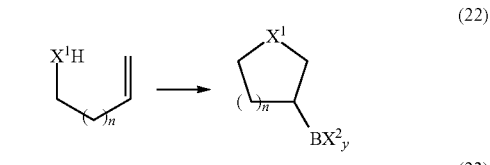

(22)

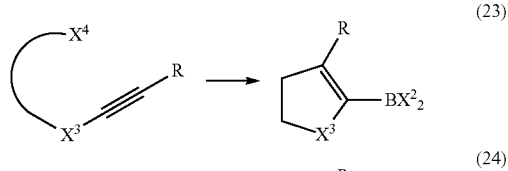

(23)

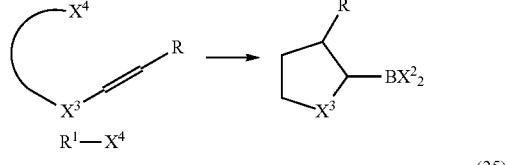

(24)

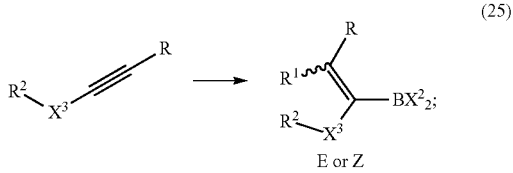

(25)

wherein $X^1$ is O, N, S, or C, wherein each of R, $R^1$, $R^2$, $R^3$, $R^4$, and $R^5$ are independently selected from: H, a carbonyl functional group, a carbocycle group, a heterocycle, a halide, or an alkyl group, wherein, optionally, $R^1$ and $R^2$ together with the carbon atoms they are attached to form a C1 to C10, aromatic or non-aromatic, cyclic moiety, wherein $X^2$ is catecholate, pinacolate, ethylene glycolate, 1,3-propanediolate, N-methyliminodiacetate, 2,2'-azanediyldiethanolate, fluoride, or chloride, wherein n is 0 to 8, wherein y is from 1 to 3, wherein $X^3$ is C, O, N, or S, and wherein $X^4$ is a halogen, trifluoroacetic acid (TFA), tosylate (OTs), mesylate (OMs), or triflate (OTf);

wherein the reagent in each Scheme (1) to (25) is reacted with a salt of $BX^2$ to form the organoboron compound(s) shown in each Scheme (1) to (25).

2. The method of claim 1, wherein each of R, $R^1$, $R^2$, $R^3$, and $R^4$ are independently selected from: H, ester, ketone, aldehyde, phenyl, naphthyl, furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, carbazole, fluoride, chloride, bromide, iodide, methyl, ethyl, vinyl, allyl, propyl, butyl, trifluoromethyl, or pentafluoroethyl.

3. The method of claim 1, where the reaction is described by: Scheme (2) or Scheme (5).

4. The method of claim 1, where the reaction is described by: Scheme (3) or Scheme (6), wherein $R^4$ is selected from H, a carbonyl functional group, a carbocycle group, a heterocycle, a halide, or an alkyl group.

5. The method of claim 1, where the reaction is described by: Scheme (8) or Scheme (11).

6. The method of claim 1, where the reaction is described by: Scheme (9) or Scheme (12), wherein $R^5$ is selected from H, a carbonyl functional group, a carbocycle group, a heterocycle, a halide, or an alkyl group.

7. The method of claim 1, where the reaction is described by: Scheme (14) or Scheme (17).

8. The method of claim 1, where the reaction is described by: Scheme (15) or Scheme (18), wherein $R^5$ is selected from H, a carbonyl functional group, a carbocycle group, a heterocycle, a halide, or an alkyl group.

9. The method of claim 1, where the reaction is described by: Scheme (20) or Scheme (22), wherein $R^5$ is selected from H, a carbonyl functional group, a carbocycle group, a heterocycle, a halide, or an alkyl group.

10. The method of claim 1, where the reaction is described by: Scheme (1) or Scheme (4).

11. The method of claim 1, where the reaction is described by: Scheme (7) or Scheme (10).

12. The method of claim 1, where the reaction is described by: Scheme (13) or Scheme (16).

13. The method of claim 1, where the reaction is described by: Scheme (23) or Scheme (24).

14. The method of claim 1, where the carbonyl functional group is a moiety selected from: an ester, a ketone, an amide, or an aldehyde, each of which is substituted or unsubstituted.

15. The method of claim 1, where the carbocycle or heterocycle group is a moiety selected from: phenyl, naphthyl, furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, or carbazole, each of which is substituted or unsubstituted.

16. The method of claim 1, where the alkyl group is selected from: methyl, ethyl, vinyl, allyl, propyl, butyl, trifluoromethyl, or pentafluoroethyl, each of which is substituted or unsubstituted.

17. A composition, comprising: an organoboron compound represented by one of the following structures:

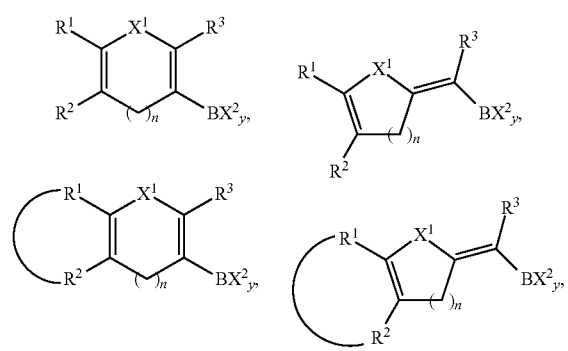

-continued
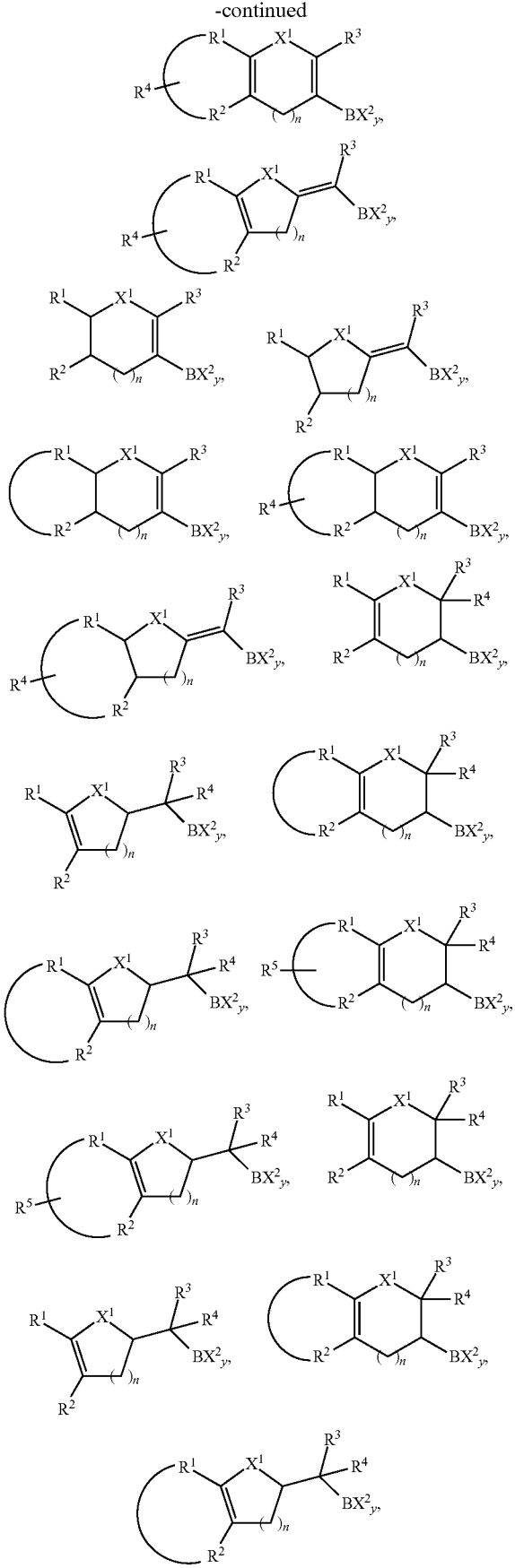
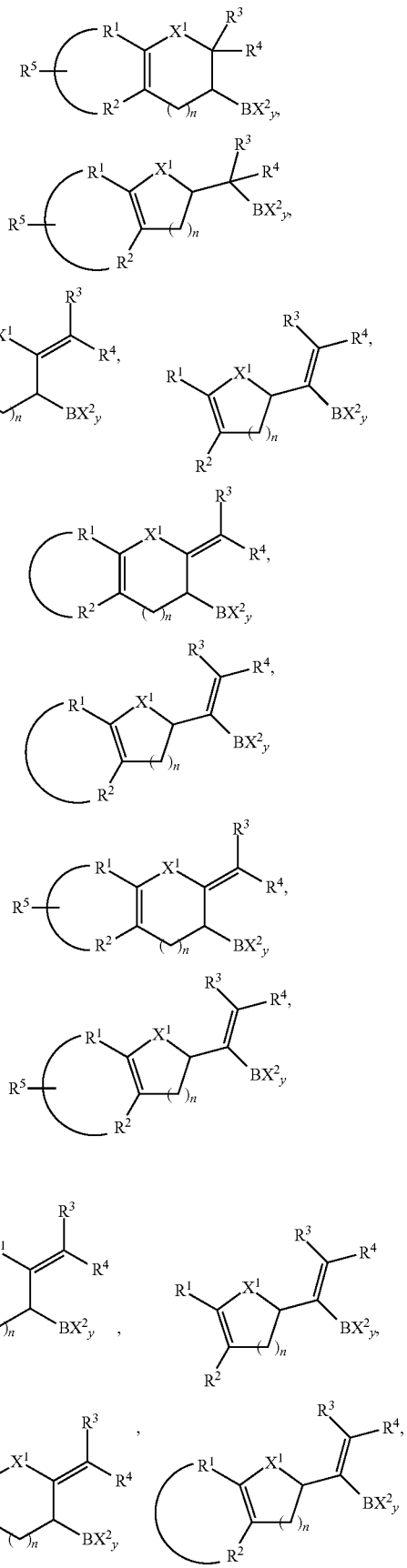

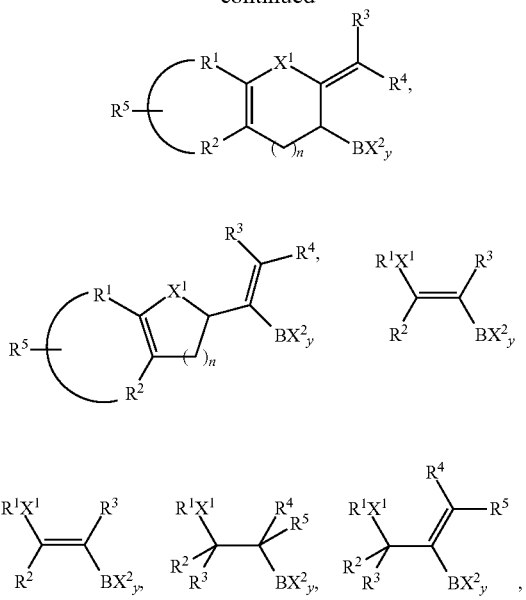

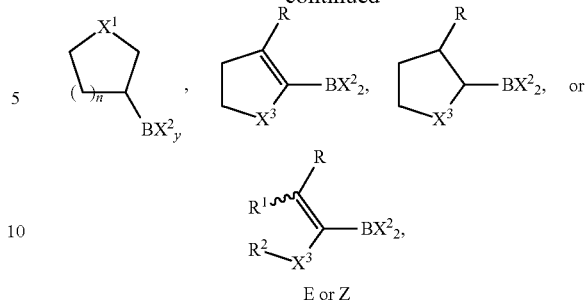

or E or Z, N, S, or C wherein each of R, $R^1$, $R^2$, $R^3$, $R^4$, and $R^5$ are independently selected from: H, a carbonyl functional group, a carbocycle group, a heterocycle, a halide, or an alkyl group, wherein, where shown, $R^1$ and $R^2$ together with the carbon atoms they are attached to form a cyclic moiety, wherein $X^2$ is catecholate, pinacolate, ethylene glycolate, 1,3-propanediolate, N-methyliminodiacetate, 2,2'-azanediyldiethanolate, fluoride, or chloride, wherein n is 0 to 8, and wherein y is from 1 to 3, wherein $X^3$ is selected from the group consisting of: C, O, N, and S.

* * * * *